United States Patent
Akao

(10) Patent No.: US 10,358,686 B2
(45) Date of Patent: Jul. 23, 2019

(54) LEATHER OR LEATHER ARTICLE AND METHOD FOR PRODUCING SAME, HEXAVALENT CHROMIUM TREATMENT AGENT, METHOD FOR TREATING HEXAVALENT CHROMIUM IN CRUDE LEATHER OR CRUDE LEATHER ARTICLE

(71) Applicant: CITIZEN WATCH CO., LTD., Tokyo (JP)

(72) Inventor: Yuji Akao, Tokyo (JP)

(73) Assignee: CITIZEN WATCH CO., LTD., Nishitokyo-Shi, Tokyo (JP)

(*) Notice: Subject to any disclaimer, the term of this patent is extended or adjusted under 35 U.S.C. 154(b) by 133 days.

(21) Appl. No.: 15/501,487

(22) PCT Filed: Jul. 29, 2015

(86) PCT No.: PCT/JP2015/071509
§ 371 (c)(1),
(2) Date: Feb. 3, 2017

(87) PCT Pub. No.: WO2016/021461
PCT Pub. Date: Nov. 2, 2016

(65) Prior Publication Data
US 2017/0233835 A1  Aug. 17, 2017

(30) Foreign Application Priority Data
Aug. 4, 2014 (JP) ................. 2014-158647

(51) Int. Cl.
*C14C 11/00* (2006.01)
*A62D 3/37* (2007.01)
(Continued)

(52) U.S. Cl.
CPC ............. *C14C 11/00* (2013.01); *A62D 3/37* (2013.01); *C07D 307/33* (2013.01);
(Continued)

(58) Field of Classification Search
CPC .... A62D 3/37; A62D 2101/43; C07D 311/72; C07D 307/33; C07C 39/08; C07C 39/10;
(Continued)

(56) References Cited

U.S. PATENT DOCUMENTS

| 2005/0072339 A1 | 4/2005 | Jardine et al. |
| 2010/0203327 A1 | 8/2010 | Inoue et al. |

(Continued)

FOREIGN PATENT DOCUMENTS

| CN | 101784679 A | 7/2010 |
| CN | 101815809 A | 8/2010 |

(Continued)

OTHER PUBLICATIONS

English Translation (Aug. 28, 2018) of the DE Patent No. 198 60 610 A1.*

(Continued)

*Primary Examiner* — Eisa B Elhilo
(74) *Attorney, Agent, or Firm* — Sughrue Mion, PLLC

(57) ABSTRACT

An object of the invention is to provide a heat-resistant hexavalent chromium removal agent, which is capable of remaining in a leather or leather article for a long period of time and stably detoxifying hexavalent chromium over the long term even when a leather or leather article contains hexavalent chromium, and a leather or leather article, in which the hexavalent chromium content is less than 3 ppm. The leather or leather article of the present invention contains at least: an organic compound (A) having a structure shown in chemical formula (1) and hydroxyphenyl but not aldehyde and carboxyl, which organic compound has a property to reduce hexavalent chromium to trivalent chromium; and trivalent chromium, and the hexavalent chromium content determined in accordance with ISO 17075: 2008-02 is less than 3 ppm.

33 Claims, 1 Drawing Sheet

(51) Int. Cl.
*C07D 311/72* (2006.01)
*C07D 307/33* (2006.01)
*C14C 3/06* (2006.01)
*C14C 9/04* (2006.01)
*A62D 101/43* (2007.01)

(52) U.S. Cl.
CPC .............. *C07D 311/72* (2013.01); *C14C 3/06* (2013.01); *C14C 9/04* (2013.01); *A62D 2101/43* (2013.01)

(58) Field of Classification Search
CPC ........... C07C 39/14; C07C 69/84; C14C 3/06; C14C 11/00
See application file for complete search history.

(56) References Cited

U.S. PATENT DOCUMENTS

| | | |
|---|---|---|
| 2010/0212542 A1 | 8/2010 | Nojima |
| 2010/0275380 A1 | 11/2010 | Zortzel et al. |
| 2010/0325811 A1 | 12/2010 | Kashiwagura et al. |
| 2011/0078862 A1 | 4/2011 | Kashiwagura et al. |
| 2011/0132498 A1 | 6/2011 | Nojima et al. |
| 2012/0231249 A1 | 9/2012 | Fukukawa et al. |
| 2014/0023555 A1 | 1/2014 | Monzyk et al. |

FOREIGN PATENT DOCUMENTS

| | | |
|---|---|---|
| CN | 102027139 A | 4/2011 |
| CN | 102719572 A | 10/2012 |
| CN | 102782160 A | 11/2012 |
| CN | 103848981 A | 6/2014 |
| DE | 19860610 A1 | 7/2000 |
| DE | 10028142 A1 | 12/2001 |
| DE | 10031548 A1 | 1/2002 |
| EP | 0512946 A1 | 11/1992 |
| JP | 2003-10676 A | 1/2003 |
| JP | 2008-231388 A | 10/2008 |
| JP | 2008-272552 A | 11/2008 |
| JP | 2010-082539 A | 4/2010 |
| JP | 5302327 B2 | 10/2013 |
| WO | 02/000941 A1 | 1/2002 |
| WO | 2007/063047 A1 | 6/2007 |
| WO | 2011/061945 A1 | 5/2011 |
| WO | 2012135594 A1 | 10/2012 |

OTHER PUBLICATIONS

STIC Search Report dated Aug. 27, 2018.*
English Transaltion (Aug. 28, 2018) of the Patent No. DE 19860610 A1.*
Database CA [Online], Chemical Abstracts Service, Jan. 1, 2012, Feng Yuan et al., "Inhibition effect for the Cr(VI) formation in leather with four kinds of antioxidants", XP002776925, retrieved from Zhongguo Pige (2012), 41(13), 10-11, 16, total 1 page.
K.J. Sreeram et al., "Sustaining tanning process through conservation, recovery and better utilization of chromium", Resources, Conservation and Recycling, Elsevier, vol. 38, No. 3, 2003, pp. 185-212.
Communication dated Feb. 9, 2018, from European Patent Office in counterpart application No. 15830021.0.
International Search Report for PCT/JP2015/071509 dated Oct. 20, 2015 [PCT/ISA/210].
Written Opinion for PCT/JP2015/071509 dated Oct. 20, 2015 [PCT/ISA/237].
Communication dated Mar. 5, 2018 issued by the State Intellectual Property Office of People's Republic of China in counterpart application No. 201580041943.1.
Extended European Search Report dated Apr. 26, 2018 issued by the European Patent Office in counterpart application No. 15830021.0.
G. Devikavathi et al., "Prevention of Carcinogenic Cr (VI) formation in leather—A three pronged approach for leather products", Indian Journal of Chemical Technology, vol. 21, Jan. 2014, pp. 7-13.
Communication dated Nov. 15, 2018, from Koean Intellectual Property Office in counterpart application No. 10-2017-7004604.
Communication dated Aug. 27, 2018 issued by the State Intellectual Property Office of the People's Republic of China in counterpart application No. 201580041943.1
Communication dated Mar. 19, 2019 from the State Intellectual Property Office of the P.R.C. in application No. 201580041943.1.

* cited by examiner

[Fig. 1]
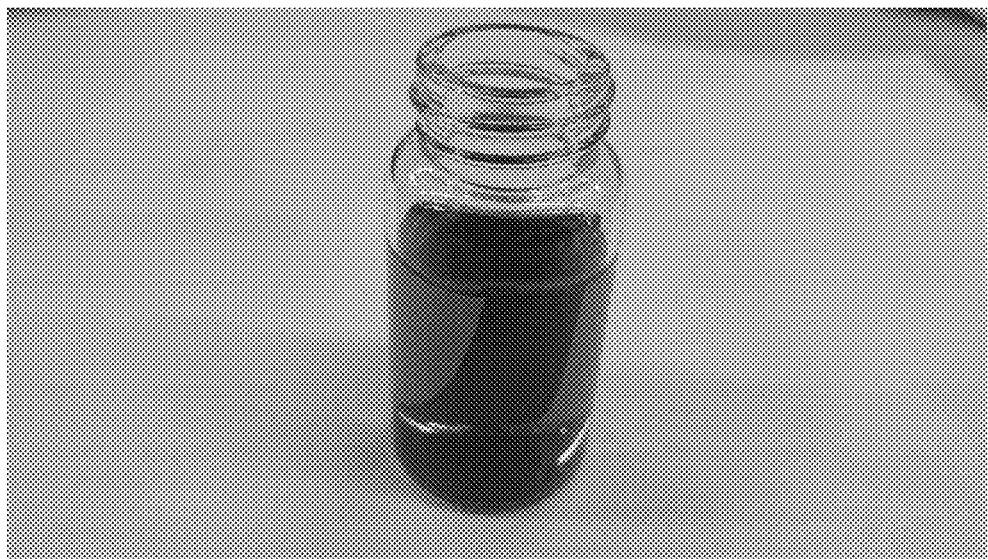
[Fig. 2]

LEATHER OR LEATHER ARTICLE AND METHOD FOR PRODUCING SAME, HEXAVALENT CHROMIUM TREATMENT AGENT, METHOD FOR TREATING HEXAVALENT CHROMIUM IN CRUDE LEATHER OR CRUDE LEATHER ARTICLE

CROSS REFERENCE TO RELATED APPLICATIONS

This application is a National Stage International of Application No. PCT/JP2015/071509 filed Jul. 29, 2015, claiming priority based on Japanese Patent Application No. 2014-158647 filed Aug. 4, 2014, the contents of all of which are incorporated herein by reference in their entirety.

FIELD OF THE INVENTION

The present invention relates to a leather or leather article with a reduced hexavalent chromium content, a method for producing the same, a hexavalent chromium treatment agent, a method for producing the treatment agent, and a method for treating hexavalent chromium in a crude leather or crude leather article. More specifically, the present invention relates to a hexavalent chromium treatment agent containing a compound having 1,2,3-trihydroxyphenyl and a leather or leather article treated with the treatment agent.

BACKGROUND OF THE INVENTION

Leather articles are used in various products such as watchbands and handbags. In particular, the look of leather increases commodity values of watchbands and handbags, increasing the level of consumer satisfaction. Also, it is needless to say that such goods are designed to allow leathers to directly touch the skin, enhancing the added value of products.

It is necessary to make a large leather sheet in advance to produce such leather articles. The skin of a desirable animal such as crocodile or cow is obtained for producing a leather. As the obtained skin has poor durability for use, it is subjected to tanning. As a result of tanning, it becomes possible to impart heat resistance and durability, thereby producing a leather from the skin. The thus obtained leather is dyed with a desirable color or subjected to surface shaping so as to make a leather sheet. The leather sheet is cut to a shape for intended use and processed by adhering a core material or the like using an adhesive so as to manufacture leather articles. Manufacturing of leather articles in the above manner has been widely known and traditionally employed.

Tanning is a method for obtaining a durable leather by processing the skin. In the past, tannin obtained from plants was used, but treatment with tannin is inadequate in terms of resistance, flexibility, and elasticity. In view of this, the recent trend is to use a chrome tanning agent (basic chromium sulfate) for chrome tanning that realizes high heat resistance, flexibility, and elasticity. Chrome tanning accounts for more than 90% of tanning in a global scale, indicating that it has the greatest economic importance. A hydrated chrome complex is embedded between carboxyl groups of glutamic acid and aspartic acid in the collagen peptide structure so that a soft durable leather can be obtained. Chrome tanning is widely known in the art and explained on the website of, for example, the Japanese Association of Leather Technology (JALT).

In addition to the above, Patent Document 1 discloses a method of tanning, comprising treating a leather and skin using a tanning agent containing deglycosylated iridoid and/or deglycosylated secoiridoid other than a tanning agent containing genipin.

RELATED ART DOCUMENTS

Patent Documents

Patent Document 1: JP Patent No. 5302327 (page 4, paragraph 0016)
Patent Document 2: JP 2008-231388 A

SUMMARY OF THE INVENTION

Technical Problem

High-quality leathers or leather articles having excellent heat resistance, flexibility, and elasticity are usually obtained by chrome tanning. Chrome tanning agents for chrome tanning contain chromium. Leathers or leather articles treated with such agents eventually contain large amounts of residual chromium. The content of residual chromium may vary depending on chrome tanning methods in different countries. However, the total content of chromium contained in leathers or leather articles obtained by X-ray fluorometry may be usually not less than 5000 ppm and not less than 6000 ppm or 7,000 ppm in some cases. It may be not less than 10000 ppm depending on the manufacturing process, leather or leather articles, and the like.

Although chrome tanning agents contain trivalent chromium, hexavalent chromium can be generated in the process of, for example, heating or adhesion during production of leathers or leather articles. Also, hexavalent chromium contained as an impurity in chrome tanning agents might be mixed with leathers or leather articles. When it is examined whether or not leathers or leather articles contain hexavalent chromium, the obtained results may show the presence of hexavalent chromium because trivalent chromium can be oxidized into hexavalent chromium due to light, heat, high temperature, and high humidity, in addition to hexavalent chromium contained during the production process. Trivalent chromium is non-toxic; however, hexavalent chromium is toxic, and it can cause skin irritation or allergy when coming into contact with the skin or mucous membrane, which may result in skin inflammation and tumor in severe cases. Therefore, hexavalent chromium significantly affects the human body. Even a small amount of hexavalent chromium is considered to have all hazard risks of carcinogenicity, mutagenicity, and reproductive toxicity. Hexavalent chromium is handled as a banned substance due to its toxicity.

In view of the above circumstances, EU regulations of hexavalent chromium in leathers or leather articles were published in the Officinal Journal of European Union (EU) No. 3014/2014 (Regulations (EU) No 301/2014) on Mar. 26, 2014. According to the Regulations, in consideration of impacts on the human body (especially in terms of skin irritation), it was determined to regulate leather articles containing not less than 3 mg/kg (3 ppm) of chromium oxide (IV) in a total dry weight of a leather and a leather part as of May 1, 2015 for leather articles and products which partially include a leather that comes into contact with the skin. In addition, the EN ISO 17075 standard method is currently available as an exclusive international analysis method for quantitative determination of hexavalent chromium in leathers or leather articles and listed on the Regulations ((6) of the Regulations).

Patent Document 1 describes that generation of hexavalent chromium can be inhibited by using particular tanning agents. However, in general, a combination of leather materials made by many companies is used for procurement of leather articles. For this reason, many companies conduct leather tanning, and it is not realistic to exclusively procure products treated with particular tanning agents in the process of tanning different leather articles.

Patent Document 2 describes in Example 2 that an aqueous solution of ascorbic acid was added dropwise to a tanned leather so as to detoxify hexavalent chromium. Ascorbic acid has strong reducing power and excels in safety and immediate effectivity. Meanwhile, since ascorbic acid is easily decomposed, when ascorbic acid is stored in a state of being dissolved in a solvent, it is likely to have been deactivated. Therefore, ascorbic acid might not be available for practical use. In addition, an aqueous solution of ascorbic acid is water repellent and hard to penetrate the interior of a highly lipophilic leather or leather article. Further, since ascorbic acid is highly water-soluble, it can be easily run off with the sweat and atmospheric moisture (e.g., dew or rain) from a leather or leather article. As a result, it is difficult to allow ascorbic acid to remain in leathers or leather articles, which may cause hexavalent chromium in the leathers or leather articles to leach into the environment or to be exposed to humans due to sweat and atmospheric moisture. It is therefore impossible to stably maintain a feature of reducing hexavalent chromium over the long term. In particular, it is impossible to detoxify hexavalent chromium generated as a result of oxidization of trivalent chromium in leathers or leather articles with ascorbic acid.

Further, as chrome tanning usually includes a heating step, a treatment agent, which is capable of maintaining reducing power during heating so as to be used during leather manufacturing, has been awaited.

In view of the above, an object of the present invention is to provide a heat-resistant hexavalent chromium removal agent, which is capable of remaining in a leather or leather article for a long period of time and stably reducing hexavalent chromium to, for example, trivalent chromium over the long term so as to detoxify hexavalent chromium even when a leather or leather article contains hexavalent chromium, and a leather or leather article, in which the hexavalent chromium content is reduced to a level that complies with the Regulations (EU) No 301/2014 with the use of the agent. Another object of the present invention is to provide a leather or leather article, in which the hexavalent chromium content determined in accordance with ISO 17075: 2008-02 is less than 3 ppm, and preferably not more than 2 ppm for increased safety. Note that the lower limit is 0 ppm.

According to the present invention, a leather or leather article before treated with the hexavalent chromium treatment agent of the present invention is referred to as a "crude leather or crude leather article," and a leather or leather article after treated with the agent is simply referred to as a "leather or leather article" in some cases. Before and after the treatment with the treatment agent, the total content of chromium contained in a leather or leather article obtained by x-ray fluorometry does not vary and it is usually not less than 5000 ppm and not less than 6000 ppm or 7,000 ppm in some cases. It may be not less than 10000 ppm depending on the manufacturing process.

Solution to Problem

The hexavalent chromium treatment agent of the present invention contains at least an organic compound (A) shown in the following chemical formula 1 including carbon atoms, oxygen atoms, and hydrogen atoms and having a hydroxyl group coupled to the center carbon atom that forms a single bond with an adjacent carbon atom and a double bond with another adjacent carbon atom, the compound acting to reduce hexavalent chromium to trivalent chromium.

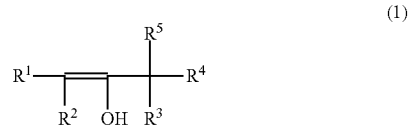

(1)

In formula (1), $R^1$, $R^2$, $R^3$, $R^4$ and $R^5$ are each independently a substituent composed of C, H, and O, and preferably have a carbonyl group, which is an unsaturated bond, but do not have reactive functional groups such as aldehyde and carboxyl. Also, $R^1$, $R^2$, $R^3$, $R^4$ and $R^5$ preferably do not have nitrogen-containing groups such as amine and isocyanate and sulfur-containing groups such as sulfate. $R^1$ or $R^2$ and $R^3$, $R^4$, or $R^5$ may bind to each other to form a ring. Further, the hexavalent chromium treatment agent of the present invention is sometimes referred to as a "hexavalent chromium removal agent."

The organic compound (A) preferably has the structure shown in the chemical formula (1) and hydroxyl but not reactive functional groups such as aldehyde and carboxyl in its structure.

In addition, the hexavalent chromium treatment agent preferably contains an organic compound (B) having the structure shown in chemical formula 1 but not hydroxyphenyl, aldehyde, and carboxyl, the compound acting to reduce hexavalent chromium to trivalent chromium, in addition to the organic compound (A). Also, the compound (B) preferably does not have nitrogen-containing groups such as amine and isocyanate and sulfur-containing groups such as sulfate.

The leather or leather article of the present invention contains: at least an organic compound (A) having the structure shown in the above chemical formula (1) and hydroxyphenyl but not oxygen-containing groups such as aldehyde and carboxyl, the compound acting to reduce hexavalent chromium to trivalent chromium; and trivalent chromium. As the leather or leather article contains the organic compound (A), the hexavalent chromium content determined in accordance with ISO 17075: 2008-02 is adjusted to less than 3 ppm and preferably not more than 2 ppm. The trivalent chromium content is not particularly limited as it varies depending on leathers or leather articles; however, it is usually not less than 4000 ppm and sometimes not less than 4500 ppm.

Examples of the organic compound (A) or (B) include the following compounds (shown in chemical formulae (2) to (14)) and derivatives thereof. It is preferable to use a mixture of these compounds in the present invention.

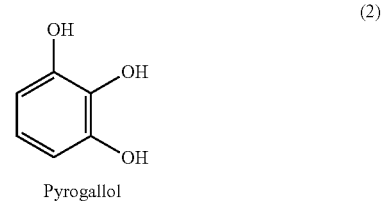

Pyrogallol (2)

-continued

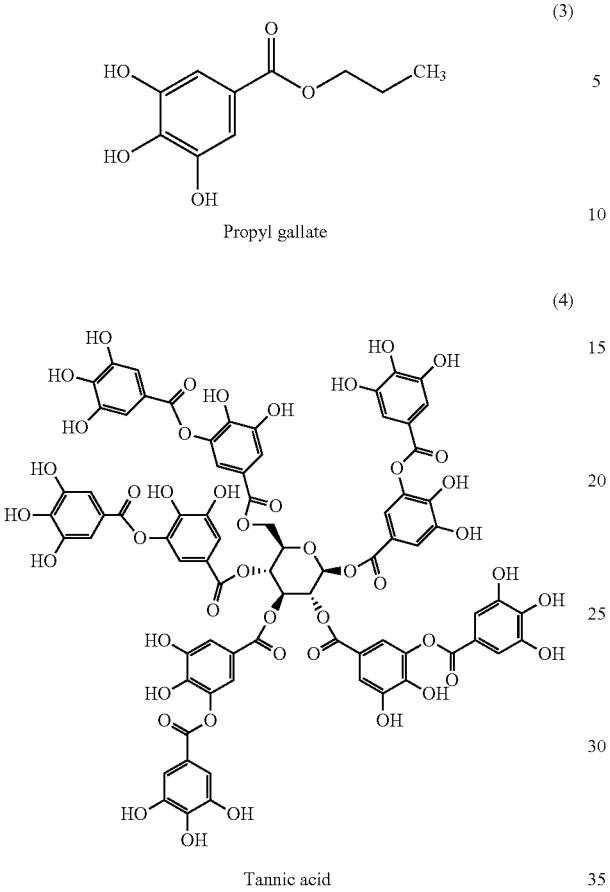

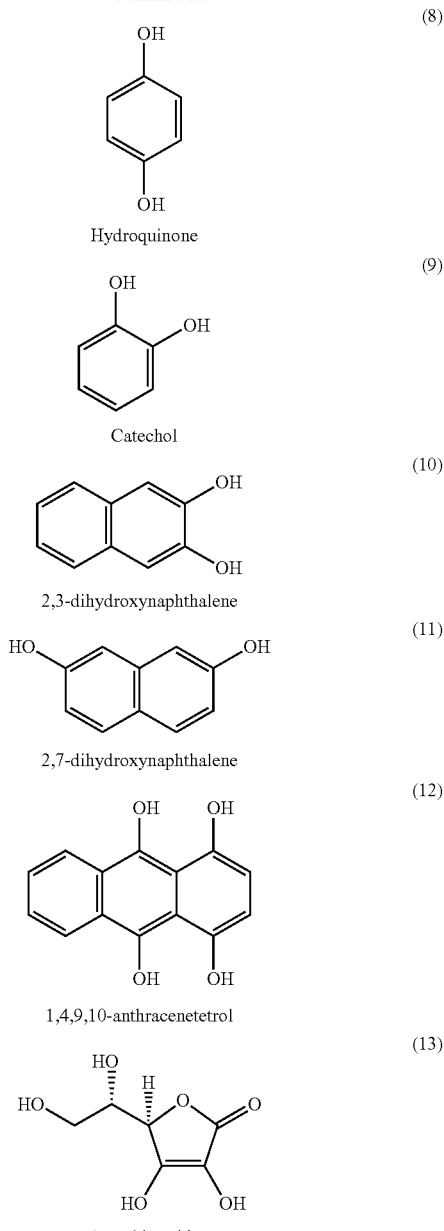

Preferably, the leather or leather article of the present invention contains a hexavalent chromium treatment agent. Regarding a method for adding the hexavalent chromium treatment agent, a leather or leather article is preferably immersed in or coated with a hexavalent chromium treatment solution obtained by diluting the hexavalent chromium treatment agent with water, an organic solvent, or a mixed solvent thereof. Regarding the method for adding the hexavalent chromium removal agent, a leather or leather article is preferably immersed in or coated with a hexavalent chromium treatment solution obtained by diluting the hexavalent chromium removal agent with a hexane and/or heptane solvent used as an organic solvent. Preferably, the hexavalent chromium treatment agent is represented by the above formula (14). Regarding the method for adding the hexavalent chromium treatment agent, it is also possible to dissolve the hexavalent chromium treatment agent in an adhesive to be used for producing a leather article so as to allow the leather article to contain the hexavalent chromium treatment agent in order to obtain a non-toxic leather article.

A leather article is preferably a leather watchband.

Advantageous Effects of Invention

The hexavalent chromium treatment agent of the present invention is characterized by immediate effectivity, long-term stable retention, long-term reducibility, and excellent heat resistance in a leather or leather article. Therefore, by using the treatment agent, it is possible to detoxify a leather or leather article containing hexavalent chromium and prevent generation of hexavalent chromium for a long period of time. In addition, as the hexavalent chromium treatment agent remains in leathers or leather articles treated therewith, it is possible to prevent generation of hexavalent chromium in use even after processed into products by customers, thereby enabling continuous detoxification. Accordingly, as non-toxic leathers can be provided, it becomes possible to commercialize a product designed in a free style with a high product value by freely using leathers procured as materials from many leather manufacturers.

Leather articles obtained using the hexavalent chromium treatment agent do not contain toxic hexavalent chromium that could induce skin irritation, allergy, and the like so as to cause skin inflammation or tumor in severe cases. Therefore, human body-friendly or environmentally friendly products can be provided.

According to the present invention, a leather or leather article, in which toxic hexavalent chromium can be detoxified until the effects and purposes of leathers or leather products are achieved, can be obtained.

Even if the leather or leather article of the present invention is exposed to sweat and atmospheric moisture (e.g., dew or rain), toxic hexavalent chromium does not leach out for a long period of time. As a result, it is possible to provide a human body-friendly and environmentally-friendly products.

BRIEF DESCRIPTION OF THE DRAWINGS

FIG. 1 is a digital camera image showing colorability of the cow leather used in Example 34.

FIG. 2 is a digital camera image showing colorability of the cow leather used in Example 35.

DETAILED DESCRIPTION OF THE INVENTION

The present invention is specifically described below.

The hexavalent chromium treatment agent of the present invention contains an organic compound capable of acting on toxic hexavalent chromium to chemically change it to a non-toxic compound. For example, such compound can reduce hexavalent chromium to non-toxic trivalent chromium.

Examples of generally known reducing agents include lithium aluminium hydride, sodium borohydride, hydrazine, dibutyl aluminum hydride, oxalic acid, and formic acid. If such typical reducing agents are used, various problems would arise.

When lithium aluminum hydride is used, the agent is a strong reducing agent in the powder form that reacts violently with water to produce hydrogen, meaning that it is flammable and dangerous. In general, leathers and leather articles are often brought into contact with the skin (sweat) or exposed to rain and the like. Therefore, such flammable substance is unacceptable for use.

When sodium borohydride is used, as the agent is slightly hygroscopic and therefore easily decomposed with water, it should be hermetically sealed and stored. An aqueous solution produced by moisture due to sweat, rain, or the like is strongly basic because the agent is a decomposition product. Therefore, such aqueous solution adversely affects the skin or mucous membrane. As the agent is decomposed under acidic and neutral conditions, it must be stored in an alkaline solution. It is difficult to handle the agent because it is decomposed with water to generate hydrogen.

Hydrazine is a colorless liquid with an ammonia-like odor. If it is exposed to air, it generates smoke and therefore it should not be used. It is easily dissolved in water and has a strong reducibility. It is also easily decomposed and flammable, which is difficult in terms of handling.

When dibutyl aluminum hydride is used, the agent is a colorless liquid, but it is vulnerable to moisture. Therefore, it needs to be stored and used under an inert gas atmosphere, meaning that it is difficult to use the agent in the general atmosphere.

When oxalic acid is used, the agent is toxic because it strongly binds to calcium ions in the body. Therefore, the agent is designated as a non-medical deleterious substance in accordance with the Poisonous and Deleterious Substances Control Act. The use of such toxic substance is inconsistent with the object of the present invention. Therefore, the agent is unacceptable for use.

When formic acid is used, a liquid or vapor of a formic acid solution is harmful for the skin and eyes, giving an unrecoverable damage especially for the eyes. In addition, if formic acid is inhaled, it might cause damage such as pulmonary edema. Therefore, formic acid is unacceptable for use. In addition to the above, as formic acid is considered to adversely affect the liver or kidney as a result of chronic exposure or to be a source of allergy, the use of formic acid is inconsistent with the object of the present invention. Therefore, the agent is unacceptable for use.

In consideration of the above, the present applicant examined a variety of hexavalent chromium treatment agents that can be used for leathers or leather articles. As a result, the present applicant found compounds that meet the object of the present invention. This has led to the completion of the present invention.

The organic compounds (A) and (B) contained in the hexavalent chromium treatment agent of the present invention have a feature of treating hexavalent chromium, involving a basic feature of detoxifying hexavalent chromium. In addition, when a leather or leather article treated with the compounds is in contact with the skin, they do not cause adverse effects such as rough skin and do not have toxicity. Further, it is preferable for the compounds (A) and (B) not to decompose each other due to their own reducibility and not to react and interfere with each other. Preferably, such compounds are stable compounds having a basic skeleton shown in chemical formula (1) and composed of C, H, and O atoms.

The organic compound shown in chemical formula (1) above does not have functional groups such as aldehyde and carboxyl. Preferably, it also does not have nitrogen-containing groups such as amine and isocyanate and sulfur-containing groups such as sulfate. These functional groups have reactivity, which might cause an unexpected reaction during the use of a leather or leather article. Therefore, the functional groups are not appropriate for the hexavalent chromium removal agent of the present invention. The organic compound can produce a compound, which acts on hexavalent chromium to generate a compound that is not detected as hexavalent chromium, thereby detoxifying hexavalent chromium.

[Organic Compound (A)]

The organic compound (A) has a structure shown in chemical formula (1) above and hydroxyphenyl shown in chemical formula (15) below. As the compound has the functional group, it has immediate effectiveness, remains stably for a long period of time, shows long-term reducibility, and has excellent heat resistance in a leather or leather article. Therefore, generation of hexavalent chromium is suppressed over the long term. Also, when it is contained in a leather or leather article, it cannot be easily decomposed by moisture of sweat, rain, or the like. The reason why the compound has such excellent effects is unclear; however, collagen that is a major leather component is usually chemically cross-linked via tanning to stabilize the compound. Hydroxyphenyl in the organic compound (A) is retained for a long period of time because it significantly interacts with collagen, while on the other hand, it is not completely incorporated into collagen and forms an island having a sea-island structure. Thus, hydroxyphenyl is considered to be incorporated with a degree of freedom so as to have reducibility. As the organic compound (A) is used in a leather or leather article, it is preferably a highly safe compound that has less environmental impacts.

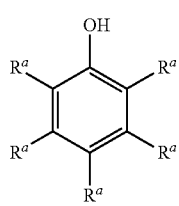

(15)

In chemical formula (15), $R^a$ represents a monovalent or divalent group. Examples of a monovalent group include a hydrogen atom, a hydrocarbon group, and an oxygen-containing group. Examples of a divalent group include a divalent hydrocarbon group and a divalent oxygen-containing group. Of these, a hydrogen atom, a monovalent hydrocarbon group, a divalent hydrocarbon group, or a hydroxyl group is preferable because compatibility to a leather or leather article can be obtained. $R^a$ may be independently the same or different from each other but may be joined together adjacently to form an aromatic or aliphatic ring. Also, $R^a$ may bind to $R^a$ of a different hydroxyphenyl group. Preferably, not all $R^a$ represent a hydrogen atom at the same time. Dihydroxyphenyl or trihydroxyphenyl is preferable, and 1,2,3-trihydroxyphenyl is more preferable so that the compound (A) stably shows improved immediate effectivity and long-term excellent reducibility in a leather or leather article.

Preferably, the hydrocarbon group is C1-C20 hydrocarbon. Specific examples include C1-C20 alkyl, C7-C20 arylalkyl, and C6-C20 aryl or substituted aryl. Examples of hydrocarbon groups include methyl, ethyl, n-propyl, isopropyl, allyl, n-butyl, isobutyl, sec-butyl, t-butyl, amyl, n-pentyl, neopentyl, n-hexyl, n-heptyl, n-octyl, n-nonyl, n-decanyl, 3-methylpentyl, 1,1-diethylpropyl, 1,1-dimethylbutyl, 1-methyl-1-propylbutyl, 1,1-propylbutyl, 1,1-dimethyl-2-methylpropyl, 1-methyl-1-isopropyl-2-methylpropyl, cyclopentyl, cyclohexyl, cycloheptyl, cyclooctyl, norbornyl, adamantyl, phenyl, o-tolyl, m-tolyl, p-tolyl, xylyl, isopropylphenyl, t-butylphenyl, naphthyl, biphenyl, terphenyl, phenanthryl, anthracenyl, benzyl, and cumyl. Also, oxygen-containing groups such as methoxy, ethoxy, and phenoxy can be included in hydrocarbon groups (e.g., alkoxy). In addition, examples of hydrocarbon groups further include unsaturated carboxylic acid esters (note that if the unsaturated carboxylic acid is dicarboxylic acid, it may be a monoester or diester) such as methyl ester, ethyl ester, n-propyl ester, isopropyl ester, n-butyl ester, isobutyl ester, and (5-norbornene-2-yl) ester.

Examples of oxygen-containing groups include hydroxyl.

Examples of the organic compound (A) include:

the compounds of chemical formulae (2) to (12) and (14);

phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, BHT (dibutylhydroxytoluene), BHA (butylhydroxyanisole), 2-phenylphenol, 3-phenylphenol, 4-phenylphenol, 3,5-diphenylphenol, 2-naphthylphenol, 3-naphthylphenol, 4-naphthylphenol, 4-trithylphenol, 2-methylresorcinol, 4-methylresorcinol, 5-methylresorcinol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, thymol, isothymol, 1-naphthol, 2-naphthol, 2-methyl-1-naphthol, 4-methoxy-1-naphthol, and 7-methoxy-2-naphthol;

dihydroxynaphthalene such as 1,5-dihydroxynaphthalene, 1,7-dihydroxynaphthalene, or 2,6-dihydroxynaphthalene;

tetrahydroxynaphthalene such as 1,3,6,8-tetrahydroxynaphthalene;

3-hydroxy-naphthalene-2-methyl carboxylate, 9-hydroxyanthracene, 1-hydroxypyrene, 1-hydroxyphenanthrene, 9-hydroxyphenanthrene, bisphenol fluorene, and phenolphthalein;

benzophenone derivatives such as 2,3,4-trihydroxybenzophenone and 2,2',3,4-tetrahydroxybenzophenone;

tannins such as catechol tannin, pyrogallol tannin, tannin from *Rhus chinensis*, gallic acid tannin, and phlorotannin;

flavonoids such as anthocyanin, rutin, quercetin, fisetin, daidzein, hesperidin, chrysin, flavonol, and hesperetin;

catechins such as catechin, gallocatechin, catechin gallate, epicatechin, epicalocatechin, epicatechin gallate, epigallocatechin gallate, procyanidin, and theaflavin;

curcumin and lignan;

acylated rhododendrols such as rhododendrol [4-(p-hydroxyphenyl)-2-butanol], acetyl rhododendrol, hexanoyl rhododendrol, octanoyl rhododendrol, dodecanoyl rhododendrol, tetradecanoyl rhododendrol, hexdecanoyl rhododendrol, octadecanoyl rhododendrol, 4-(3-acetoxybutyl)

phenyl acetate, 4-(3-propanoyloxybutyl)phenylpropanoate, 4-(3-octanoyloxybutyl) phenyloctanoate, and 4-(3-palmitiloxybutyl)phenylparmitate;

rhododendrol alkyl ethers such as 4-(3-methoxybutyl) phenol, 4-(3-etoxibutyl)phenol, and 4-(3-octyloxybutylphenol;

rhododendrol glycosides such as rhododendrol-D-glucoside (α or β form), rhododendrol-D-galactoside (α or β form), rhododendrol-D-xyloside (α or β form), and rhododendrol-D-maltosid (α or β form); and α-tocopherol, β-tocopherol, γ-tocopherol, and δ-tocopherol.

Also, derivatives of the above examples such as a compound having alkoxyl and an ester compound are included. Specific examples include pyrogallol-1,3-dimethylether, pyrogallol-1,3-diethylether, and 5-propylpyrogallol-1-methylether.

Examples of the organic compound (A) include a compound having a structure shown in chemical formula (2) above 1,2,3-trihydroxybenzene skeleton) and a derivative thereof. These compounds have a feature of removing hexavalent chromium.

One example of the derivative is a compound shown in chemical formula (2) having a substituent such as a hydrocarbon group or an oxygen-containing group at position 4, 5, or 6. Preferable examples of such substituent include C1-C20 hydrocarbon, C1-C20 alkoxy, and a C1-C20 esterified compound. More preferable examples of the substituent include C1-C10 hydrocarbon, C1-C20 alkoxy, and a C1-C10 esterified compound. These groups are as per stated above. Note that the same applies to compounds and derivatives described below. Examples include gallic acid ester of a compound shown in chemical formula (3) above, a compound shown in chemical formula (4) above having a plurality of structures shown in chemical formula (2) in a single molecule, a and derivative of the compound. Examples include tannins such as catechol tannin, pyrogallol tannin, tannin from *Rhus chinensis*, gallic acid tannin, and phlorotannin.

As stated above, it is possible to introduce a substituent at position 4, 5, or 6 in a manner appropriate for each substituent. For example, if a compound is dissolved in an ester-based solvent, an ester group is introduced to increase compatibility.

In the present invention, the compound (A) preferably contains: (i) gallic acid ester; and (ii) at least one compound selected from tannic acid and a derivative thereof. More preferably, it contains: (i) gallic acid ester; and (ii) tannic acid.

Gallic acid ester has a relatively small molecular weight and therefore it is considered likely to bleed from leathers or leather articles. Meanwhile, as gallic acid ester has a partial structure of tannic acid, it suitably interacts with tannic acid and a derivative thereof while maintaining reducing power, which makes gallic acid ester difficult to bleed. Gallic acid ester has reducing power even in leathers or leather articles and therefore it has high immediate effectivity. Reducing power of gallic acid ester is stronger than that of tannic acid but weaker than that of ascorbic acid. Therefore, even after ascorbic acid loses reducing power when decomposed, gallic acid ester shows reducing power over the long term (and then it again becomes able to reduce chromium ions that have been oxidized to hexavalent chromium). Gallic acid ester is strongly resistant against moisture of sweat, rain, or the like and unlikely to be decomposed in leathers or leather articles.

Tannic acid and a derivative thereof are highly bulky and originally used for tanning treatment. That is, they have a high affinity to collagen and the like in leathers or leather articles and therefore they are unlikely to bleed, thereby maintaining reducing power over the long term in leathers or leather articles. Hence, they can prevent generation of hexavalent chromium over the long term. In addition, tannic acid and a derivative thereof are hypoallergenic to humans (skin) and therefore highly safe. Although tannic acid and a derivative thereof exert reducing power in a time-lagged manner, compared with ascorbic acid and gallic acid ester, they have a high affinity to leathers and leather articles and are unlikely to be decomposed. Therefore, they can maintain reducing power until the effects and purposes of leather articles are achieved, compared with ascorbic acid and gallic acid ester.

Therefore, if leathers or leather articles contain the above compounds, the compounds can significantly penetrate leathers or leather articles, remain therein for a long term, and exert stable reducing power over the long term. Further, there is concern that strong reducibility of polyphenols might cause browning or loss of color. However, as the compounds are incorporated into leathers or leather articles before loss of color, color fading or discoloration is unlikely to take place and the color and texture of leathers or leather articles are less likely to be impaired, which is preferable.

In addition, although a hydroxyl group is located at positions 1, 2, and 3 in chemical formula (2) above, similar effects can be obtained with a compound having a skeleton in which a hydroxyl group is introduced at positions 1, 2, and 4 (chemical formula (5)) and a compound having a skeleton in which a hydroxyl group is introduced at positions 1, 3, and 5 (chemical formula (6)). Also, derivatives of such compounds have similar effects.

Further, although three hydroxyl groups have been introduced into an aromatic ring in chemical formula (2) above, a compound having one hydroxyl group and a compound having two hydroxyl groups also have a feature of removing hexavalent chromium. For example, phenol, BHT, compounds shown in chemical formulae (7), (8), and (9), and their derivatives have the above skeletons.

Also, a compound formed with a plurality of aromatic rings bound to each other having hydroxyl groups has similar effects. Examples thereof include a compound with a naphthalene ring having one or more hydroxyl groups. Examples of such compound having two hydroxyl groups include compounds shown in chemical formulae (10) and (11). Derivatives of these compounds also have a feature of removing hexavalent chromium.

A compound of anthracene having three aromatic rings bound in series, into which one or more hydroxyl groups have been introduced at arbitrary positions, also has similar feature. One example of such compound is a compound shown in chemical formula (12). Derivatives thereof also have a feature of removing hexavalent chromium.

Examples of a compound shown in chemical formula (1) include a compound having a long-chain alkyl group and a complex ring. Such compound is highly organic and less water-soluble. Meanwhile, as it has a high affinity to organic solvents, it can be dissolved in hydrocarbon-based solvents, which is advantageous. Examples of such compound include a compound shown in chemical formula (14).

Preferable examples of a compound shown in chemical formula (1) include: catechins such as catechin, gallocatechin, catechin gallate, epicatechin, epicalocatechin, epicatechin gallate, epicalocatechin gallate, procyanidin, and theaflavin; and catechin derivatives. These catechins are excellent in terms of safety and have strong reducing power in leathers or leather articles.

[Organic Compound (B)]

An organic compound (B) has a structure shown in chemical formula (1) but does not have a hydroxyphenyl group shown in chemical formula (15). As it does not contain the hydroxyphenyl group, it is unlikely to penetrate leathers or leather articles. However, as it has a structure shown in chemical formula (1), it can appropriately reduce hexavalent chromium present on leathers or leather articles to trivalent chromium so as to detoxify hexavalent chromium. Therefore, by using the compound (B), it becomes possible to prevent hexavalent chromium ions dissolved in moisture of sweat, rain, or the like from leaching in the environment or being exposed to humans with good immediate effectivity. One example of the organic compound (B) is a heterocyclic compound. Examples of a heterocyclic compound include furan, chromen, isocromen, and xanthene. Examples of derivatives of the compound (B) include a compound shown in chemical formula (13) and a derivative thereof, erythorbic acid and a derivative thereof, and 4-hydroxyfuran-2(5H)-one. These compounds have a feature of removing hexavalent chromium.

Examples of a derivative of ascorbic acid include, but are not particularly limited to, ascorbic acid ester, ascorbic acid phosphate ester, ascorbic acid sulfate ester, ascorbic acid glucoside (2-O-α-D-glucopyranosyl-L-ascorbic acid), ascorbic acid glucosamine, and dehydroascorbic acid.

Examples of a derivative of erythorbic acid include erythorbic acid ester.

In the present invention, the organic compound (B) is preferably at least one compound selected from ascorbic and erythorbic acid and more preferably ascorbic acid. The compound cannot achieve long-term effects because it is easily decomposed, and it is likely to bleed from leathers or leather articles. However, it is hypoallergenic for humans (skin) and excellent in safety and it has high reducing power and good immediate effectivity. Therefore, by bringing a treatment agent containing the compound (B) into contact with leathers or leather articles, it becomes possible to effectively and preliminarily prevent hexavalent chromium ions from leaching in the environment or being exposed to humans. In addition, as surface detoxification can be quickly performed, the development of skin problems, allergy, etc. can be appropriately suppressed. Such compound (B) does not react with and is not compatible with the organic compound (A). Thus, the compound (B) can be appropriately mixed with the treatment agent. In addition, as the compound (B) has strong reducing power, the addition of the compound (B) enables prevention of brownish discoloration and loss of color due to the organic compound (A). Further, the compound (B) is highly degradable and thus unlikely to cause coloration and impair the color and texture of leathers or leather articles, which is preferable.

As stated above, a compound containing a basic skeleton shown in chemical formula (1) in its molecule can detoxify and remove hexavalent chromium.

[Weight Ratio of Organic Compounds (A) and (B)]

The hexavalent chromium treatment agent of the present invention contains the organic compounds (A) and (B) at a weight percent ratio ((A):(B)) of preferably 50-90:10-50, more preferably 50-80:20-50, and further preferably 50-70:30-50 (note that the sum of A and B equals to 100% by weight), which is not particularly limited as long as the effects of the present invention can be obtained. The organic compound (A) has excellent immediate effectivity but it is unlikely to penetrate leathers or leather articles, making it impossible to achieve long-term stability. Therefore, the amount of the organic compound (A) is preferably comparable to or less than that of the organic compound (B). Meanwhile, if the content of the organic compound (A) is less than 10% by weight, it might become impossible to appropriately reduce hexavalent chromium on the surfaces of the leathers or leather articles to trivalent chromium so as to detoxify hexavalent chromium.

When the hexavalent chromium treatment agent contains: (i) gallic acid ester; (ii) at least one compound selected from tannic acid and a derivative thereof; and the organic compound (B), the weight percent ratio ((i):(ii):(B)) is preferably 1-20:30-89:10-50, more preferably 3-17:33-77:20-50, and further preferably 5-15:35-65:30-50 (note that the sum of (i), (ii) and (B) equals to 100% by weight), which is not particularly limited as long as the effects of the present invention can be obtained. The weight percent of the organic compound (A) is as per described above. The organic compound (B) is preferably ascorbic acid and/or erythorbic acid so that the organic compound (B) is incompatible with the compounds (i) and (ii) and thus is not incorporated into the compound (ii), thereby making it possible to appropriately reduce the surfaces of leathers or leather articles. The compounds (i) and (ii) mainly act to reduce hexavalent chromium inside of leathers or leather articles. Ascorbic acid, propyl gallate, and tannic acid used herein satisfy the standards of international safety regarding their concentrations in leathers or leather articles in terms of carcinogenicity, skin sensitization, and skin irritation specified in the OECD Guidelines for the Testing of Chemicals. The compound (i) has high reducing capacity but it is relatively easily decomposed. Meanwhile, as the compound (ii) has the compound (i) as a part thereof, the compound (i) can be obtained by decomposing the compound (ii); however, the compound (ii) shows reducing capacity in a time-lagged manner, compared with ascorbic acid and gallic acid ester. Therefore, the amount of the compound (ii) is preferably greater than that of the compound (i). It is also pointed out that the compound (i) is slightly irritable to humans (skin) and relatively has colorability, compared with the compound (ii) and the organic compound (B). Therefore, it is preferable to use the compound (i) in an amount less than the amounts of the compound (ii) and the organic compound (B). When the amount of the compound (ii) is less than 1% by weight, it is impossible to rapidly detoxify hexavalent chromium in leathers or leather articles. Accordingly, untreated hexavalent chromium might be eluted on the leather surfaces if hexavalent chromium in an amount that cannot be treated with the provided amount of the organic compound (B) remains or after the organic compound (B) becomes inactive. As polyphenols have strong reducibility, there is concern of brownish discoloration or loss of color. However, when polyphenols are used at the above weight ratio, they are likely to be suitably incorporated into leathers or leather articles before loss of color. This further prevents color fading and discoloration and is unlikely to impair the color or texture of leathers or leather articles, which is preferable. In addition, in the case of the above ratio, polyphenols are likely to be dissolved in both water and organic solvents, which is preferable. The above treatment solution achieves long-term stability, which is preferable.

Next, a method for obtaining leathers or leather articles using a hexavalent chromium removal agent and a hexavalent chromium treatment method are described below.

The leather or leather article of the present invention can be obtained by a production method, comprising bringing a crude leather containing hexavalent chromium or a crude leather article containing hexavalent chromium into contact with a hexavalent chromium treatment agent. The hexavalent chromium content in a leather or leather article obtained by the method is less than 3 ppm when determined in accordance with ISO 17075: 2008-02, and the total content of chromium in a leather or leather article is not less than 5000 ppm when determined by X-ray fluorometry.

Examples of the leather or leather article of the present invention include, but are not particularly limited to, products obtained by chrome tanning of cow skin, sheep skin, goat skin, pig skin, horse skin, deer skin, kangaroo skin, ostrich skin, crocodile skin, lizard skin, snake skin, bird skin, and fish skin, and processed products thereof. Examples of processed products include shoes, clothing, hats, gloves, belts, wallets, business card cases, watchbands, bags, sofa, cushion, cushion covers, book covers, pen cases, cell phone cases, planners, key cases, automotive interiors, glasses cases, and tool cases.

The hexavalent chromium treatment agent of the present invention detoxifies hexavalent chromium in leathers or leather articles obtained via chrome tanning in the tanning step. Thus, it can be used for any of the above examples.

One example of treatment in the tanning step is described below. In general, the raw skin stripped from an animal is used. Fat, proteins, and the like are removed from the skin. Then, the skin is subjected to the tanning step such as chrome tanning. Thereafter, the skin is washed, dehydrated in a drum, and processed using a roll coater. Thus, a leather (e.g., leather sheet) is obtained. According to the present invention, for example, the hexavalent chromium treatment agent is introduced into the drum to detoxify hexavalent chromium. In addition, as many holes are formed on the roll coater, it is also possible to carry out detoxification by, for example, spraying the hexavalent chromium treatment agent together with water through the holes. In the above cases, it is preferable to use, as the hexavalent chromium treatment agent, a treatment solution consisting of water or a treatment solution containing water and C1-C3 alcohol described below.

It is also possible to carry out detoxification by bringing an untreated leather used as a raw leather material (e.g., a leather sheet, which is herein referred to as "crude leather" in some cases) into contact with the hexavalent chromium treatment agent. The method describe below can be used for such contact.

A desired leather article can be obtained by cutting a purchased leather sheet into a suitable shape and attaching a core material thereto or bonding the leather sheet by sewing or using an adhesive. Note that an untreated leather article is also referred to as a crude leather article according to the present invention.

For example, a watchband is obtained by bonding a leather cut in a band shape to both sides of a core material using an adhesive and heating the obtained product.

In some cases, a finished product is obtained by hemming a leather article for the improvement of the texture.

Upon production of a leather article, if a leather sheet is subjected to tanning using chromium, it contains chromium. In such case, chromium is mostly trivalent chromium. However, the leather sheet is exposed to physical stress (e.g., light, heat, high temperature and humidity) at different situations during storage, import, transport, marketing, handling, and the like, which might result in generation of toxic hexavalent chromium. If a leather sheet used as a raw material contains hexavalent chromium and a leather article is obtained by processing the leather sheet, a leather article (e.g., a watchband) containing toxic hexavalent chromium is eventually obtained. In view of this, it is ideal to preliminarily detoxify a leather sheet that has been subjected to chrome tanning using the hexavalent chromium removal agent or the present invention.

A leather sheet can be detoxified using the hexavalent chromium removal agent at any timing before or after cutting the leather sheet to a specified size.

Hexavalent chromium can be detoxified by bringing a crude leather containing hexavalent chromium or a crude leather article containing hexavalent chromium into contact with the hexavalent chromium treatment agent. The contact means is not particularly limited as long as the effects of the present invention can be obtained. However, examples of such means include spraying, atomizing, dipping, coating, and immersion. As the organic compounds (A) and (B) show strong reducing capacity on the surface of a crude leather or crude leather article, hexavalent chromium can be treated by bringing the hexavalent chromium treatment agent into direct contact with the surface. In a case in which the hexavalent chromium removal agent is allowed to deeply penetrate a leather or leather article so as to maintain long-term reducibility, it is preferable to treat the leather or leather article with a treatment solution prepared by dissolving the hexavalent chromium removal agent in a single solvent such as water, C1-C3 alcohol (propanol, isopropanol (IPA), methanol, or ethanol), butanol, acetone, methyl ethyl ketone (MEK), toluene, xylene, N,N-dimethylformamide (DMF), hexane, or heptane, a mixed solvent of water and such organic solvent, or a volatile organic solvent obtained by mixing several organic solvents. As a solvent, at least one solvent selected from the group consisting of water, C1-C3 alcohol, hexane, and heptane is preferably used, and two or more solvents selected therefrom are more preferably used to obtain a suitable treatment solution. If possible, it is desirable to avoid using hydrocarbon-based solvents such as toluene because they are excellent in terms of penetration through leathers or leather articles but harmful to humans. The treatment solution is applied to a leather sheet before or after cutting by spraying or brushing, surface rubbing using a cloth dipped in the treatment solution, or immersion so that the leather is allowed to contain the hexavalent chromium removal agent. The surface of a leather or leather article is very delicate and vulnerable. Therefore, it is preferable to apply the hexavalent chromium removal agent by spraying. Thus, hexavalent chromium is detoxified and a non-toxic leather can be obtained.

It would be also possible to treat, for example, finished leather articles available in the market, which contain hexavalent chromium. In this case, a leather article part is removed from a watch or the like, and the leather article is treated by spraying or brushing, surface rubbing using a cloth dipped in the treatment solution containing the hexavalent chromium treatment agent, or immersion so that the leather is allowed to contain the hexavalent chromium removal agent.

In one embodiment of the present invention, the hexavalent chromium treatment agent also includes the treatment solution.

The content of the organic compound (A) in the hexavalent chromium treatment solution is not particularly limited; however, it is preferably about 0.01% to 10.0% (by weight), more preferably about 0.1% to 7.0% (by weight), further preferably about 0.3% to 5.0% (by weight), and furthermore preferably about 0.5% to 3.0% (by weight), and yet further preferably about 0.5% to 2.0% (by weight) in the treatment solution (100% by weight). The above range is preferable because color fading or discoloration of leathers or leather articles can be particularly reduced.

The sum of the contents of the organic compounds (A) and (B) in the hexavalent chromium treatment solution is not particularly limited; however, it is preferably about 0.01% to 10.0% (by weight), more preferably about 0.1% to 7.0% (by weight), further preferably about 0.3% to 5.0% (by weight), and furthermore preferably about 0.5% to 3.0% (by weight), and yet further preferably about 0.5% to 2.0% (by weight) in the treatment solution (100% by weight). The above range is preferable because color fading or discoloration of leathers or leather articles can be particularly reduced.

The hexavalent chromium treatment agent comprising the treatment solution is preferably able to permeate leathers or leather articles. If the treatment solution contains an organic solvent, it can suitably penetrate leathers or leather articles because they are relatively fat-soluble. If it contains water and C1-C3 alcohol, safety and handleability can be further improved, and therefore, the treatment solution can penetrate leathers or leather articles without impairing designability such as color or texture and causing color fading or brownish discoloration, which is more preferable.

The hexavalent chromium treatment agent comprising the treatment solution is not particularly limited as long as the effects of the present invention can be obtained. However, in order to allow the hexavalent chromium treatment agent to rapidly penetrate leathers or leather articles for detoxification, the kinematic viscosity at 25° C. is preferably 0.001 (cSt) to less than 5 (cSt), more preferably 0.01 (cSt) to 4.5 (cSt), and further preferably 0.05 (cSt) to 4.3 (cSt), and yet further preferably 0.1 (cSt) to 4.0 (cSt). JP 2008-272552 A discloses an agent for treating soil contaminated with hexavalent chromium (aqueous solution) containing ascorbic acid, which is thickened with a thickening agent to a viscosity of not less than 5 cP. As disclosed in JP 2008-272552 A, if the viscosity of the treatment agent is less than 5 cP, permeability becomes too high to achieve uniform permeation into soil. Therefore, such treatment agent with a viscosity of less than 5 cP cannot be used for treating hexavalent chromium in soil. As collagen that is a main component of leathers or leather articles is chemically cross-linked so as to be stable, the treatment agent with a viscosity of less than 5 cP might not permeate leathers or leather articles, which is not preferable.

It is preferable to use, as a solvent for a treatment solution, water alone especially when treating a leathers or leather article characterized by its design in order to maintain the color and texture in terms of designability and not to cause color fading and brownish discoloration.

The organic compound (B) tends to be relatively water soluble while the organic compound (A) tends to be relatively hydrophobic because it has a phenyl group. Therefore, as a solvent used as a treatment solution should be able to appropriately dissolve the organic compound (A) and also the organic compound (B), the solvent preferably includes a polar solvent, although a polar solvent may cause loss of color more often than a non-polar solvent. More preferably, C1-C3 alcohol is used. Further preferably, IPA is used. This is because high handleability is achieved, leathers or leather articles relatively maintain the color and texture in terms of designability, color fading and brownish discoloration do not occur, and IPA is excellent in terms of miscibility and solubility in a variety of organic compounds. In addition, the treatment solution preferably further contains water such that the organic compound (B) can be easily dissolved. In a case in which the treatment solution contains water and alcohol, the percent weight ratio (alcohol:water) is preferably 20-80:20-80, more preferably 30-70:30-70, and further preferably 40-60:40-60, at which the organic compounds (A) and (B) can be appropriately dissolved and mixed, and treatment can be carried out while leathers or leather articles relatively maintain the color and texture in terms of designability, and color fading and brownish discoloration do not occur (note that the sum of both is 100% by mass). If a solvent consists of water, it might not penetrate leathers or leather articles because leathers or leather articles are water-repellent and relatively hydrophobic (lipophilic). However, a treatment solution containing water and C1-C3 alcohol can deeply penetrate leathers or leather articles without impairing designability because it has moderate volatility. Also, if the content of alcohol exceeds 80% by weight, it is not preferable in consideration of the flash point of alcohol because a fire might occur in factories. If IPA is used as the alcohol, the content thereof is preferably not more than 60% by weight in consideration of the flash point. Meanwhile, if the content of the alcohol is less than 20% by weight, the solubility in leathers or leather articles might not be improved.

In a case in which ascorbic acid and/or erythorbic acid is used as the organic compound (A), the compound is unlikely to be dissolved in a polar solvent other than water because it is highly water-soluble. In a case in which gallic acid ester and/or a tannic acid derivative is used as the organic compound (B), such compound is unlikely to be dissolved in water because the compound is relatively highly hydrophobic. In particular, gallic acid ester and/or a tannic acid derivative is unlikely to be dissolved in a non-polar solvent. In addition, tannic acid is amphiphilic.

A solvent used as a treatment solution is preferably a non-polar organic solvent rather than water in order to maintain long-term reducibility in leathers or leather articles. More preferably, the solvent includes at least one solvent selected from hexane and heptane because they do not extract coloring components and are less likely to cause color change than other non-aqueous solvents due to their high volatility. Further preferably, hexane is used because of its rapid drying rate and good workability. The above solvents are highly volatile and can appropriately dissolve the relatively hydrophobic organic compound (A) in a short period of time and penetrate relatively fat-soluble leathers or leather articles. However, as the solvent is exclusively a highly volatile and flammable organic solvent, careful handling of the solvent is necessary particularly when a large amount of the solvent is required for the method for treating hexavalent chromium by immersion because a fire might occur in factories. Also, as it is difficult to dissolve a relatively hydrophilic organic compound in a non-polar organic solvent, it is necessary to appropriately select an organic compound that can be used. The side brought into contact with the treatment solution is preferably the back side of a leather or leather article in consideration of influence on designability. In such case, it is preferable to treat the front side of a leather or leather article using water alone or a treatment solution containing water and a polar solvent. Also, in a case in which the organic compound (A) is relatively water-soluble, it is preferable to use C1-C3 alcohol in consideration of compatibility with hexane and/or heptane, although it is less likely to dissolve the organic compound (A) than water. It is more preferable to use IPA because it has less impacts on leathers or leather articles and safety and handleability can be obtained. A mixed solvent of a non-polar solvent and the alcohol is preferable because it has less impacts on leathers or leather articles, and therefore, it can deeply penetrate leathers or leather articles and can be used for a wide range of leathers and leather articles, which results in high productivity. Further, as IPA is less volatile than hexane and heptane, even if the solvent evaporates during working, it does not cause the treatment solution to precipitate, allowing working for a long period of time. Furthermore, a mixed solvent is preferable as it can dissolve a variety of organic compounds. In a case in which the treatment solution contains C1-C3 alcohol and hexane and/or heptane, the weight percent ratio (alcohol:hexane and/or heptane) is preferably 20-90:10-80, more preferably 35-85: 15-65, and further preferably 45-80:20-55, at which the treatment solution has less impacts on leathers or leather articles, and it can relatively appropriately dissolve and mix the organic compounds (A) and (B) (note that the sum of both is 100% by mass). If the alcohol content exceeds 90% by weight, it might cause loss of color on the surface of a leather or leather article while it does not affect quality.

The thus treated leathers and leather articles contain the hexavalent chromium removal agent of the present invention. Hexavalent chromium can be detoxified with the hexavalent chromium removal agent containing hexavalent chromium in leathers or leather articles if non-toxic chromium is changed to toxic hexavalent chromium. That is to say, leathers or leather articles treated with the hexavalent chromium removal agent can stably maintain a non-toxic state even after processed into final products.

In addition, when a leather article is produced, a leather may be adhered to the front side and the back side of a non-leather core material (e.g., resin in many cases) using an adhesive. It is possible to add the hexavalent chromium removal agent to the adhesive so as to detoxify hexavalent chromium using the adhesive. In a case in which the hexavalent chromium removal agent containing an adhesive is used, the hexavalent chromium removal agent is present between a leather used for the front side and a leather used for the back side. Accordingly, hexavalent chromium does not migrate between the front side and the back side, thereby preventing contamination, which is advantageous. The above case is particularly effective when a tanned leather, which contains chromium on the front side but not on the back side, is used. The above case is advantageous in that hexavalent chromium cannot penetrate a part of the back side, which is brought into contact with the skin.

The hexavalent chromium removal agent contains at least an organic compound shown in chemical formula 1 including C, O, and H and having a hydroxyl group coupled to the center carbon atom that forms a single bond with an adjacent carbon atom and a double bond with another adjacent carbon atom, which organic compound has a property to reduce the hexavalent chromium to trivalent chromium.

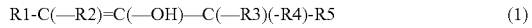

R1-C(—R2)=C(—OH)—C(—R3)(-R4)-R5          (1)

(R1, R2, R3, R4, and R5 are each independently a substituent composed of C, H, and O and containing carbonyl, which is an unsaturated bond, but not functional groups such as aldehyde and carboxyl.)

The organic compound is the above compound (any of the compounds shown in chemical formulae (2) to (14)), a derivative thereof, or a mixture thereof.

A leather article contains the hexavalent chromium removal agent.

Regarding the method for adding the hexavalent chromium removal agent, a leather is immersed in or coated with a hexavalent chromium treatment solution obtained by diluting the hexavalent chromium removal agent with water, an organic solvent, or a mixed solvent thereof.

Regarding the method for adding the hexavalent chromium removal agent, a leather is immersed in or coated with a hexavalent chromium treatment solution obtained by diluting the hexavalent chromium removal agent with a hexane and/or heptane solvent used as an organic solvent.

A leather article is obtained using the method for adding the hexavalent chromium removal agent.

The hexavalent chromium removal agent is represented by chemical formula (14).

The method for adding the hexavalent chromium removal agent comprises dissolving the hexavalent chromium removal agent in an adhesive to allow a leather to contain the hexavalent chromium removal agent.

The leather article is a leather watchband.

The leather or leather article contains at least: an organic compound (A) having a structure shown in chemical formula (1) above and hydroxyphenyl but not aldehyde and carboxyl, which organic compound has a property to reduce the hexavalent chromium to trivalent chromium; and trivalent chromium, and the hexavalent chromium content determined in accordance with ISO 17075: 2008-02 is less than 3 ppm.

The hexavalent chromium treatment agent contains at least: (A) an organic compound having a structure shown in chemical formula (1) above and hydroxyphenyl but not aldehyde and carboxyl, the organic compound acting to reduce hexavalent chromium to trivalent chromium; and (B) an organic compound having a structure shown in chemical formula (1) but not hydroxyphenyl, aldehyde, and carboxyl, the organic compound acting to reduce hexavalent chromium to trivalent chromium.

The hexavalent chromium treatment agent contains at least: (A) an organic compound having a structure shown in chemical formula (1) above and hydroxyphenyl but not aldehyde and carboxyl, the organic compound acting to reduce hexavalent chromium to trivalent chromium; and at least two solvents selected from the group consisting of water, C1-C3 alcohol, hexane, and heptane, and the hexavalent chromium treatment agent is capable of permeating a leather or leather article.

The method for treating hexavalent chromium contained in a crude leather or crude leather article comprises bringing a crude leather containing hexavalent chromium or a crude leather article containing hexavalent chromium into contact with the hexavalent chromium treatment agent.

The method for producing a leather or leather article comprises bringing a crude leather containing hexavalent chromium or a crude leather article containing hexavalent chromium into contact with the hexavalent chromium treatment agent, and the hexavalent chromium content determined in accordance with ISO 17075: 2008-02 is less than 3 ppm.

EXAMPLES

The present invention is described in more detail below based on the following Examples. However, the present invention is not limited to the Examples.

The compounds shown in chemical formulae (2) to (14) were prepared as examples of the compound shown in chemical formula (1).

The compounds were evaluated as described below.
(1) Kinematic Viscosity (cSt)

Kinetic viscosity of a hexavalent chromium treatment solution was determined at 25.0° C. using an Ubbelohde viscometer and a mixed solvent of IPA and water (1 vol:1 vol) as a solvent.

(2) Total Chromium Content (ppm)

The total chromium content in a leather or leather article was determined using an energy dispersive fluorescent X-ray analyzer (JSX-3202EV ELEMENT ANALYZER; JEOL Ltd.).

In addition, as reference samples, the following were used: JSX3000 series reference sample 1, JSX3000 series reference sample 2, and JSX3000 series energy calibration reference sample (JEOL Ltd.). The content was determined using JSX starter and selecting the PlasticD3 mode based on QuickManual provided by JEOL Ltd. (EY07007-J00, J00 EY07007G, Issue of August 2007).

Reference Example 1

(Confirmation of Reactivity to Hexavalent Chromium)

10 ml of a 1/60 mol/l aqueous solution of potassium dichromate (hexavalent chromium) was added to a container. The compound shown in chemical formula (2) was added thereto so that the content of the compound was 4 times by mole the hexavalent chrome content, followed by stirring at room temperature. At this time, the color of the solution changed from orange to red purple.

Quantitative Determination of Total Cr in the Obtained Solution by ICP Emission Spectrometry.

The sample was decomposed by heating with sulfuric acid and nitric acid and dissolved in dilute nitric acid during heating so as to result in a predetermined volume. The resulting solution was subjected to determination of total Cr by ICP emission spectrometry (device: ICP emission spectrometer SPS3000; SII NanoTechnology Inc.) to obtain the Cr content in the sample.

Quantitative Determination of Hexavalent Chromium by Ion Chromatography

The sample was diluted 1000-fold with ultrapure water. The dilution was stirred by shaking for 20 minutes and filtered through a cation ion exchange cartridge (OnGuard2H; Thermo Fisher Scientific). This treatment liquid was subjected to quantitative determination by ion chromatography. A blank was obtained without using the sample in the same manner.

Measurement Conditions of Ion Chromatography
Device: Dionex ICS-3000
Sample injection volume: 10 µl
Eluent: 15 mM potassium hydroxide
Separation column: 2 mm 250 mm IonPac AS23
Column temperature: 35° C.
Detector: Electric conductivity meter
Analysis results: total chromium content: 1720 µg/g (1st measurement); 1720 µg/g (2nd measurement)
Average: 1720 µg/g Hexavalent chromium content: below the detection limit (1st measurement); below the detection limit (2nd measurement)

The above results revealed that hexavalent chromium contained at the beginning (total chromium content) was treated with the organic compound (A) so as to be detoxified.

Reference Example 2-1

A 1/60 mol/l dichromate solution in an amount of 0.5 g was added dropwise to 0.6 g of filter paper (No. 131; ToyoRoshiKaisha, Ltd.) to contaminate the filter paper with hexavalent chromium. The filter paper was dried at room temperature (about 25° C.). Thus, a contaminated medium was obtained.

The compound shown in chemical formula (2) in an amount of 0.3 g was dissolved in 10 g of pure water to prepare a hexavalent chromium treatment solution. Subsequently, 1 g of this treatment solution was applied to the medium contaminated with hexavalent chromium using a brush and dried at room temperature.

The resulting medium was submitted to a certification body for ISO 17075: 2008-02 for determination of the hexavalent chromium content. As a result, hexavalent chromium was not present and not detected at or below the detection limit (<2 ppm). In the present invention, the term "detection limit" is also referred to as "determination limit."

The above results indicate that the medium contaminated with chromium hexavalent was successfully detoxified using the compound shown in chemical formula (2).

Reference: As a result of examination of the contaminated medium in accordance with ISO 17075: 2008-02, 830 ppm of hexavalent chromium was detected.

Reference Example 2-2

A 1/60 mol/l dichromate solution in an amount of 0.5 g was added dropwise to 0.6 g of filter paper (No. 131; ToyoRoshiKaisha, Ltd.) to contaminate the filter paper with hexavalent chromium. The filter paper was dried at room temperature (about 25° C.). Thus, a contaminated medium was obtained.

The compound shown in chemical formula (2) in an amount of 0.3 g was dissolved in 10 g of pure water to prepare a hexavalent chromium treatment solution. Subsequently, 1 g of this treatment solution was applied to the medium contaminated with hexavalent chromium using a brush and dried at 120° C., which exceeds heating temperatures that can be expected in manufacturing of leather articles.

The resulting medium was submitted to a certification body for ISO 17075: 2008-02 for determination of the hexavalent chromium content. The results indicated that hexavalent chromium was not present and not detected at or below the detection limit.

The above results indicate that it is possible to detoxify the medium contaminated with chromium hexavalent using the compound shown in chemical formula (2) even using the heating step that can be expected in manufacturing of leather articles.

Reference Example 2-3

A 1/60 mol/l dichromate solution in an amount of 0.5 g was added dropwise to 0.6 g of filter paper (No. 131; ToyoRoshiKaisha, Ltd.) to contaminate the filter paper with hexavalent chromium. The filter paper was dried at room temperature (about 25° C.). Thus, a contaminated medium was obtained.

The compound shown in chemical formula (2) in an amount of 0.3 g was dissolved in 10 g of pure water to prepare a hexavalent chromium treatment solution. Subsequently, 1 g of this treatment solution was applied to the medium contaminated with hexavalent chromium using a brush and dried at 120° C., which exceeds heating temperatures that can be expected in manufacturing of leather articles.

In order to examine whether it is possible to keep leather articles non-toxic under heating conditions, an acceleration test was conducted with a heat history of 120° C. for two hours.

The resulting medium was submitted to a certification body for ISO 17075: 2008-02 for determination of the hexavalent chromium content. The results indicated that hexavalent chromium was not present and not detected at or below the detection limit.

The above results indicate that it is possible to detoxify the medium contaminated with chromium hexavalent using the compound shown in chemical formula (2) even using the heating step that can be expected in manufacturing of leather articles, and the detoxifying effect can be maintained.

Reference Examples 3-1 to 3-3

Tests similar to those described in Reference Examples 2-1 to 2-3 were conducted except that the compound shown in chemical formula (4) was used instead of the compound shown in chemical formula (2). As a result, no hexavalent chromium was detected at or below the detection limit in each case.

The above results revealed that the compound shown in chemical formula (4) has effects similar to those of the compound shown in chemical formula (2).

Reference Examples 4-1 to 4-3

Tests similar to those described in Reference Examples 2-1 to 2-3 were conducted except that 10 g of ethanol was used instead of 10 g of purified water. As a result, no hexavalent chromium was detected at or below the detection limit in each case.

The above results revealed that hexavalent chromium treatment can be carried out via the application of the compound dissolved in ethanol and the treatment effect is persistent.

Reference Examples 5-1 to 5-3

Tests similar to those described in Reference Examples 2-1 to 2-3 except that 10 g of a mixed solvent consisting of 20 parts by weight of toluene, 40 parts by weight of MEK, 15 parts by weight of acetone, and 5 parts by weight of DMF was used instead of 10 g of purified water. As a result, no hexavalent chromium was detected at or below the detection limit in each case.

The above results revealed that hexavalent chromium treatment can be carried out via the application of the compound dissolved in ethanol, and the treatment effect is persistent.

Reference Examples 6-1 to 6-3 and 7-1 to 7-3

Tests similar to those described in Reference Examples 4-1 to 4-3 and 5-1 to 5-3 were conducted except that the compound shown in chemical formula (3) was used instead of the compound shown in chemical formula (2). As a result, no hexavalent chromium was detected at or below the detection limit in each case.

The above results revealed that the compound shown in chemical formula (3) has effects similar to those of the compound shown in chemical formula (2).

Reference Examples 8-1 to 8-3, 9-1 to 9-3, 10-1 to 10-3, 11-1 to 11-3, 12-1 to 12-3, 13-1 to 13-3, 14-1 to 14-3, 15-1 to 15-3, and 16-1 to 16-3

Tests similar to those described in Reference Examples 5-1 to 5-3 were conducted except that the compounds shown in chemical formulae (5) to (13) were used. As a result, no hexavalent chromium was detected at or below the detection limit in each case.

The above results revealed that hexavalent chromium can be treated with the compounds shown in chemical formulae (5) to (13) as well, and the treatment effect is persistent.

Reference Examples 17-1 to 17-3 and 18-1 to 18-3

Tests similar to those described in Reference Examples 4-1 to 4-3 were conducted except that the compound shown in chemical formula (14) was used instead of the compound shown in chemical formula (2), and hexane and heptane were used as solvents. As a result, no hexavalent chromium was detected at or below the detection limit in each case.

The above results revealed that the compound shown in chemical formula (14) has effects similar to those of the compound shown in chemical formula (2).

Reference Examples 19-1 to 19-3

Tests similar to those described in Reference Examples 5-1 to 5-3 were conducted except that a mixture of the compounds shown in chemical formulae (4) and (6) in an amount of 50 parts by weight each was prepared and 0.3 g of the mixture was used. As a result, no hexavalent chromium was detected at or below the detection limit in each case.

The above results revealed that hexavalent chromium can be treated and detoxified even with a mixture of several compounds. In addition, as it is possible to mix several compounds, it was revealed that it is possible to mix hexavalent chromium treatment agents in an appropriate combination depending on use conditions such as a variation in solubility in a solvent for treatment of hexavalent chromium.

Example 20

Many various types of adhesives for adhering leather sheets, core materials, and the like have been commercially available. Whether mixtures of such adhesives and the hexavalent chromium treatment agent can maintain the features of the hexavalent chromium treatment agent was experimentally confirmed. In this Example, Hi-Bon 4250 (Hitachi Chemical Polymer Co., Ltd.) was used. The compound shown in chemical formula (2) in an amount of 0.3 g was dissolved in 10 g of the adhesive. The compound was easily dissolved therein. The obtained mixture remained liquid even after having been stored at room temperature for 30 days. The features of the adhesive remained unchanged. As a result, it was found that the hexavalent chromium treatment agent can be mixed with an adhesive. This was probably because the hexavalent chromium treatment agent did not contain functional groups with high reactivity such as aldehyde, amino, and carboxyl, and therefore, it did not specifically react with adhesive components and remained stable.

A crocodile leather and a cow leather were adhered to the front side and the back side of a plastic core material, respectively, using the adhesive that had been stored for 30 days at room temperature and an adhesive that was mixed immediately before use. Thus, watchbands were created. Desirable adhesion was achieved for each watchband. Thus, leather articles each having an excellent appearance were obtained as suitable watchbands.

The hexavalent chromium contents in the finished watchbands were determined in accordance with ISO-17075: 2008-02. In each case, the hexavalent chromium content was at or below the detection limit (2 ppm). Thus, non-toxic products were obtained while hexavalent chromium was not detected. In addition, leather bands created in the above manner were stored at 60° C. for 500 hours and analyzed in accordance with ISO 17075: 2008-02. In each case, it was found that hexavalent chromium was not detected (detection limit of not more than 2 ppm) and the non-toxic state was maintained.

The above results revealed that the hexavalent chromium treatment agent can be mixed with commercially available leather adhesives, and leather articles that have been finished using such mixture can be provided as non-toxic leather articles free from hexavalent chromium. No hexavalent chromium was detected (detection limit of not more than 2 ppm) even after additional heating. It was therefore found that such leather articles can be thermally stable and maintained in a non-toxic state for commercial use.

Examples 21-1 to 21-12 and Reference Examples 21-13 and 21-18

Leather sheets obtained by chrome tanning were prepared. Crocodile and cow leathers were used. The leathers were cut to the size of watchbands so that watchbands were obtained as raw materials.

Three different compounds shown in chemical formulae (2), (4), and (13) in an amount of 0.3 g each were separately dissolved in 10 g of ethanol so that three different treatment solutions each containing a different one of the compounds were prepared. The treatment solutions were applied to the leathers using a spray and dried at room temperature so that treated leather sheets were obtained.

Subsequently, 0.3 g each of three different compounds shown in chemical formulae (2), (4), and (13) were separately dissolved in 10 g of an adhesive (Hi-Bon 4250) so that three different adhesives each containing a different one of the compounds were prepared. The adhesives were applied to three types of crocodile leathers and three types of cow leathers so that watchbands (of 18 types in total) were obtained. The watchbands prepared using crocodile leathers were divided into two groups for aging evaluation and for evaluation using running water.

[Aging Evaluation]

The obtained watchbands (18 types of crocodile and cow leathers) were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

[Evaluation Using Running Water]

Immediately after 9 types of watchbands were created using crocodile leathers, they were immersed in running water without aging so as to be sufficiently impregnated with tap water (Tokyo, Japan). The resulting watchbands were aged at 60° C. for 500 hours so that the watchbands for evaluation were obtained.

For each band, the hexavalent chromium content was determined in accordance with ISO 17075: 2008-02. As a result, the watchbands obtained using the compounds shown in chemical formulae (2) and (4) were confirmed to contain hexavalent chromium at or below the detection limit (2 ppm). Therefore, the watchbands were found to be non-toxic. Meanwhile, hexavalent chromium was detected from the watchbands that had been obtained using the compound shown in chemical formula (13).

Product model numbers of the watchbands were as follows: 59-S52979 (Citizen Watch Co., Ltd.) for the cow leather; and 59-T50736 (Citizen Watch Co., Ltd.) for the crocodile leather.

The above results revealed that non-toxic watchbands (leather articles) capable of maintaining a state of being free from hexavalent chromium can be obtained using the organic compound according to the present invention. The compound shown in chemical formula (13) was found to have strong reducing power while having a tendency to be dissolved in water. Specifically, when the compound is exposed to sweat and atmospheric moisture (e.g., dew or rain), it would easily run off, which might cause toxic hexavalent chromium to be exposed to humans or to be released into the environment.

Examples 22-1 to 22-12 and Reference Examples 22-13 and 22-18

Leather sheets obtained by chrome tanning were prepared. Crocodile and cow leathers were used. The leathers were cut to the size of watchbands so that watchbands were obtained as raw materials, which were then immersed in a 1/60 mol/l potassium dichromate solution so as to be contaminated with hexavalent chromium. Due to the contamination, the hexavalent chromium content increased by about 70 ppm in the leather sheets.

Three different compounds shown in chemical formulae (2), (4), and (13) in an amount of 0.3 g each were separately dissolved in 10 g of ethanol so that three different treatment solutions each containing a different one of the compounds were prepared. The treatment solutions were applied to leathers using a spray and dried at room temperature so that treated leather sheets were obtained.

Subsequently, 0.3 g each of three different compounds shown in chemical formulae (2), (4), and (13) were separately dissolved in 10 g of an adhesive (Hi-Bon 4250) so that three different adhesives each containing a different one of the compounds were prepared. The adhesives were applied to three types of crocodile leathers and three types of cow leathers so that watchbands (of 18 types in total) were obtained. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Subsequently, the watchbands that had been aged were immersed in running water so as to be sufficiently impregnated with tap water. The resulting watchbands were aged at 80° C. for 500 hours so that the watchbands for evaluation were obtained.

For each band, the hexavalent chromium content was determined in accordance with ISO 17075: 2008-02. The watchbands obtained using the compounds shown in chemical formulae (2) and (4) were found to contain hexavalent chromium at or below the detection limit (2 ppm). Meanwhile, hexavalent chromium was detected from the watchbands that had been obtained using the compound shown in chemical formula (13).

Product model numbers of the watchbands were as follows: 59-S52979 for the cow leather; and 59-T50736 for the crocodile leather.

The above results revealed that non-toxic watchbands (leather articles) capable of maintaining a state of being free from hexavalent chromium can be obtained using the organic compound according to the present invention. The compound shown in chemical formula (13) was found to have strong reducing power; however, it was deactivated by running water, indicating that the compound is unlikely to maintain long-term reducing power. This revealed that the compound shown in chemical formula (13) is easy decomposed.

Examples 23-1 to 23-12 and Reference Examples 23-13 and 23-18

Leather sheets obtained by chrome tanning were prepared. Crocodile and cow leathers were used. The leathers were cut to the size of watchbands so that watchbands were obtained as raw materials, which were then immersed in a 1/60 mol/l potassium dichromate solution so as to be contaminated with hexavalent chromium.

The three different compounds shown in chemical formulae (2), (4), and (13) in an amount of 0.3 g each were separately dissolved in 10 g of a mixed solvent consisting of 20 parts by weight of toluene, 40 parts by weight of MEK, 15 parts by weight of acetone, and 5 parts by weight of DMF so that three different treatment solutions each containing a different one of the compounds were prepared. The treatment solutions were applied to the leathers using a spray and dried at room temperature so that treated leather sheets were obtained.

Subsequently, 0.3 g each of three different compounds shown in chemical formulae (2), (4), and (13) were separately dissolved in 10 g of an adhesive (Hi-Bon 4250) so that three different adhesives each containing a different one of the compounds were prepared. The adhesives were applied to three types of crocodile leathers and three types of cow leathers so that watchbands (of 18 types in total) were obtained. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Subsequently, the watchbands that had been aged were immersed in running water so as to be sufficiently impregnated with tap water. The resulting watchbands were aged at 80° C. for 500 hours so that watchbands for evaluation were obtained.

For each band, the hexavalent chromium content was determined in accordance with ISO 17075: 2008-02. The watchbands obtained using the compounds shown in chemical formulae (2) and (4) were confirmed to contain hexavalent chromium at or below the detection limit (2 ppm). Meanwhile, hexavalent chromium was detected from the watchbands that had been obtained using the compound shown in chemical formula (13).

Product model numbers of the watchbands were as follows: 59-S52979 for the cow leather; and 59-T50736 for the crocodile leather.

The above results revealed that non-toxic watchbands (leather articles) capable of maintaining a state of being free from hexavalent chromium can be obtained using the organic compound according to the present invention. The compound shown in chemical formula (13) was found to have strong reducing power; however, it was deactivated by running water, indicating that the compound is unlikely to maintain long-term reducing power.

Examples 24-1 to 24-12 and Reference Examples 24-13 and 24-18

Leather sheets obtained by chrome tanning were prepared. Crocodile and cow leathers were used. The leathers were cut to the size of watchbands so that watchbands were obtained as raw materials, which were then immersed in a 1/60 mol/l potassium dichromate solution so as to be contaminated with hexavalent chromium.

The three different compounds shown in chemical formulae (2), (4), and (13) in an amount of 0.3 g each were separately dissolved in 10 g of pure water so that three different treatment solutions each containing a different one of the compounds were prepared. The treatment solutions were applied to the leathers using a spray and dried at room temperature so that treated leather sheets were obtained.

Subsequently, 0.3 g each of three different compounds shown in chemical formulae (2), (4), and (13) were separately dissolved in 10 g of an adhesive (Hi-Bon 4250) so that three different adhesives each containing a different one of the compounds were prepared. The adhesives were applied to three types of crocodile leathers and three types of cow leathers so that watchbands (of 18 types in total) were obtained. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Subsequently, the watchbands that had been aged were immersed in running water so as to be sufficiently impregnated with tap water. The resulting watchbands were aged at 80° C. for 500 hours so that watchbands for evaluation were obtained.

For each band, the hexavalent chromium content was determined in accordance with ISO 17075: 2008-02. The watchbands obtained using the compounds shown in chemical formulae (2) and (4) were confirmed to contain hexavalent chromium at or below the detection limit (2 ppm). Meanwhile, hexavalent chromium was detected from the watchbands that had been obtained using the compound shown in chemical formula (13).

Product model numbers of the watchbands were as follows: 59-S52979 for the cow leather; and 59-T50736 for the crocodile leather.

The above results revealed that non-toxic watchbands (leather articles) capable of maintaining a state of being free from hexavalent chromium can be obtained using the organic compound according to the present invention. The compound shown in chemical formula (13) was found to have strong reducing power; however, it was deactivated by running water, indicating that the compound is unlikely to maintain long-term reducing power. In addition, the leather sheets were immersed in a potassium dichromate solution so as to be deeply impregnated with the solution. Thus, even the solution containing the compound shown in chemical formula (13) penetrated the leather sheets.

Examples 25-1 to 25-4

Leather sheets obtained by chrome tanning were prepared. Crocodile and cow leathers were used. The leathers were cut to the size of watchbands so as to be obtained as raw materials, which were then immersed in a 1/60 mol/l potassium dichromate solution so as to be contaminated with hexavalent chromium.

The compound shown in chemical formula (14) in an amount of 0.3 g was dissolved in 10 g of hexane, and in an amount of 0.3 g in 10 g of heptane so that treatment solutions each containing a hexavalent chromium treatment agent were prepared. These treatment solutions were applied to the leathers using a spray and dried at room temperature. Thus, two types of treated leather sheets were obtained. At this time, it was found that hexane and heptane have excellent ability to penetrate leathers and are less likely to cause color changes than other non-aqueous solvents without extracting coloring components. In particular, hexane was found to be quickly dried and excellent in workability.

Subsequently, watchbands (of 4 types in total) were obtained using an adhesive (Hi-Bon 4250) and crocodile and cow leathers. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Product model numbers of the watchbands were as follows: 59-S52979 for the cow leather; and 59-T50736 for the crocodile leather.

As a result, it was found that non-toxic watchbands (leather articles) capable of maintaining a state of being free from hexavalent chromium can be obtained using a hexavalent chromium treatment agent.

Further, it was found that harmless bands, in which hexavalent chromium has been treated to minimize changes in the leather color or texture, can be obtained using a highly organic hexavalent chromium treatment agent represented by the compound shown in chemical formula (14) and a solvent such as hexane or heptane.

Reference: When a hexavalent chromium treatment agent prepared by dissolving 0.3 g of the compound shown in chemical formula (2) in 10 g of IPA is applied to leathers repeatedly, the leather color gradually changes (loss of color). This is not problematic in practical use. However, when a product with a unique color is produced, the solvent and the hexavalent chromium treatment agent shown in Example 25 are preferable.

Example 26

The crocodile leather bands and the cow leather bands (product model no. 59-S52979 for the cow leather and product model no. 59-T50736 for the crocodile leather) each containing hexavalent chromium described in Comparative Examples 1 and 2 were prepared.

The compound shown in chemical equation (14) in an amount of 0.3 g was dissolved in 10 g of hexane, and in an amount of 0.3 g in 10 g of heptane so that treatment solutions each containing a hexavalent chromium treatment agent were prepared.

The commercially available bands were immersed in the obtained two different hexavalent chromium treatment solutions so as to be impregnated therewith, followed by drying. Thus, watchbands were obtained.

For each band, the hexavalent chromium content was determined in accordance with ISO 17075: 2008-02. Each band was confirmed to contain hexavalent chromium at or below the detection limit (2 ppm). The bands were found to be non-toxic.

As a result, it was found that harmless watchbands (leather articles) capable of maintaining a state of being free from hexavalent chromium can be obtained using a hexavalent chromium treatment agent.

Further, it was found that harmless bands, in which hexavalent chromium has been treated to minimize changes in the leather color or texture, can be obtained using a highly organic hexavalent chromium treatment agent represented by the compound shown in chemical formula (14) and a solvent such as hexane or heptane. Furthermore, hexane is superior to heptane in terms of volatility and characterized by excellent treatment performance because of short treatment time. Also, since the rate of penetration into leathers in the case of either heptane or hexane is much faster than that in the case of water, heptane or hexane is more advantageous than water that is also characterized by fewer color changes. If a hydrocarbon solvent such as the composition shown in chemical formula (4) or (13) is used, hexavalent chromium is not dissolved therein, making it impossible to obtain the treatment effects. However, if the composition shown in chemical formula (14) which comprises long-chain alkyl having at least 10 carbon atoms (and specifically 16 carbon atoms in chemical formula 14) or a derivative thereof is used, hexavalent chromium can be dissolved. As described above, a hexavalent chromium treatment agent optimal for leather articles, which has a feature of treating hexavalent chromium and causes little changes in the leather color and texture such as a feeling of touch, a treatment method using the agent, a treatment method using the same, and a leather article obtained using the same were successfully obtained in this Example.

Example 27

Leather sheets obtained by chrome tanning were prepared. Crocodile and cow leathers were used. The leathers were cut to the size of watchbands so as to be obtained as raw materials, which were then immersed in a 1/60 mol/l potassium dichromate solution so as to be contaminated with hexavalent chromium.

The compound shown in chemical formula (13) in an amount of 0.3 g was dissolved in 10 g of pure water so that a treatment solution (W) containing the organic compound (B) was prepared.

Further, 0.15 g of the compound shown in chemical formula (4) and 0.15 g of the compound shown in chemical formula (3) (0.30 g in total) were dissolved in 10 g of mixed solutions containing IPA and hexane at ratios of 8:2, 7:3, and 5:5 so that three different treatment solutions containing the hexavalent chromium treatment agents (8:2, 7:3, and 5:5) were created. The kinetic viscosity of the treatment solution containing IPA and hexane at a ratio of 5:5 was about 1.1 (cSt).

The treatment solution (W) was applied to the front sides of the leathers using a cloth moistened with the solution (W). The treatment solutions (8:2, 7:3, and 5:5) were each separately applied to the back sides of the leathers using a spray and dried. The treatment solutions (8:2, 7:3, and 5:5) sprayed on the back sides showed excellent ability to penetrate, and they were less likely to have impacts on leathers and therefore usable for many types of leathers because they contained not only IPA but also hexane as a hydrocarbon. As they are less likely to have impacts on leathers, they can be applied to an extent that sufficient amounts thereof can penetrate from the back sides to the front sides of leathers, which is desirable. Further, as the compounds shown in chemical formulae (3) and (4) were found to be more soluble in IPA than in hexane, the hexavalent chromium treatment agents did not precipitate and could be suitably used for a long period of time, even though the solvent of the treatment solutions evaporated to some extent during work. It was revealed that by mixing a hydrocarbon-based non-polar solvent with a polar solvent such as alcohol and using the mixture, it is possible to obtain a treatment solution having a feature of reducing impacts of hydrocarbon on leathers and a feature of improving solubility of a hexavalent chromium treatment agent in a polar solvent in a well-balanced manner, which is convenient for production. It was also revealed in this Example that in order to reduce impacts on leathers by adding a non-polar solvent to a polar solvent, the content of the non-polar solvent with respect to that of the polarity solvent needs to be not less than 20 wt %. (In the test in which a treatment solution (9:1) was used, product quality was acceptable; however, the leather surface looked slightly white.)

Subsequently, watchbands (of 6 types in total) were obtained using an adhesive (Hi-Bon 4250) and also using three types of crocodile leathers and three types of cow leathers subjected to front-side treatment and back-side treatment. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Subsequently, the watchbands that had been aged were immersed in running water so as to be sufficiently impregnated with tap water. The resulting watchbands were aged at 80° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm).

Product model numbers of the watchbands were as follows: 59-S52979 for the cow leather; and 59-T50736 for the crocodile leather.

As a result, it was found that non-toxic watchbands (leather articles) capable of maintaining a state of being free from hexavalent chromium can be obtained using a hexavalent chromium treatment agent. It was also found that even if the hexavalent chromium treatment agent is exposed to sweat and atmospheric moisture, it can prevent toxic hexavalent chromium from leaching out and maintain reducing power for detoxification for a long period of time.

Further, the treatment solutions used for back-side treatment of leathers was diluted with the same solvent (IPA/hexane) so that 2-fold, 3-fold, 5-fold, 10-fold, and 30-fold diluted treatment solutions were created. As stated above, crocodile and cow leathers contaminated with hexavalent chromium were subjected to top-side treatment with the treatment solution (W) and back-side treatment with the treatment solutions (2-fold, 3-fold, 5-fold, 10-fold, and 30-fold diluted treatment solutions) using a spray and dried.

Subsequently, watchbands (of 30 types in total) were obtained using an adhesive (Hi-Bon 4250) and the crocodile and cow leathers. The resulting watchbands were aged at 60° C. for 500 hours so that watchbands for evaluation were obtained.

For each band, the hexavalent chromium content was determined in accordance with ISO 17075: 2008-02. Each band was confirmed to contain hexavalent chromium at or below the detection limit (2 ppm). The bands were found to be non-toxic.

Product model numbers of the watchbands were as follows: 59-S52979 for the cow leather; and 59-T50736 for the crocodile leather.

The above results revealed that the effects of a hexavalent chromium treatment agent can be obtained if the concentration of the hexavalent chromium treatment agent in 10 g of a solvent is not less than 0.01 g, which is an appropriate level.

Comparative Examples 1 to 2

Leather sheets obtained by chrome tanning were prepared as described in Example 20. Crocodile and cow leathers were used. The leathers were cut to the size of watchbands so that watchbands were obtained as raw materials. The leathers were each adhered to a plastic core material using an adhesive (Hi-Bon 4250) in the manner described in Example 20. Thus, watchbands were created. Product model numbers of the watchbands were as follows: 59-S52979 for the cow leather; and 59-T50736 for the crocodile leather. The hexavalent chromium contents in the obtained watchbands were determined in accordance with ISO 17075: 2008-02 while the watchbands were maintained in the optimal state without aging at 60° C. because heating of the watchbands might cause generation of hexavalent chromium. As a result, even under advantageous conditions, the hexavalent chromium contents in the crocodile leather and the cow leather were detected as 8 ppm and 3 ppm, respectively.

In addition, as a result of analysis of the total chromium content of each band using a fluorescent X-ray analyzer, the chromium contents in the crocodile leather and the cow leather were 16362 ppm and 7141 ppm, respectively.

Comparative Examples 3-1 to 3-3, 4-1 to 4-3, and 5-1 to 5-3

Tests similar to those described in Reference Examples 2-1 to 2-3 were conducted except that 1,2,3-cyclohexanetriol, α-cyclodextrin, D-(+)-glucose were each used instead of the compound shown in chemical formula (2).

As a result, the chromium hexavalent content was as high as not less than 830 ppm in each case. The above results revealed that hexavalent chromium cannot be treated using similar compounds having a carbon atom with a hydroxyl group, which have similar skeletons and consist of 3 species of C, H, and O without an aldehyde or carboxyl group, if such compounds do not have the structure specified in the present invention.

Comparative Examples 6-1 to 6-3

Confirmation of Reactivity to Hexavalent Chromium 10 ml of a ¹⁄₆₀ mol/l aqueous solution of potassium dichromate (hexavalent chromium) was added to a container. 1,2,3-cyclohexanetriol, α-cyclodextrin, and D-(+)-glucose (1 g each) were separately added thereto, followed by stirring at room temperature.

As a result, hexavalent chromium remained unchanged and the characteristic ion color also remained unchanged in each solution. The above results revealed that hexavalent chromium cannot be treated using similar compounds having a carbon atom with a hydroxyl group, which have similar skeletons and consist of 3 species of C, H, and O without an aldehyde or carboxyl group, if such compounds do not have the structure specified in the present invention.

The expression of application of hexavalent chromium used herein (in the Examples and Comparative Examples) means application of hexavalent chromium using a brush, a spray, a sponge roller, or the like. Cow leathers are called calf leathers in the leather industry. In the experiments of the present invention, cow leathers are referred to as calf leathers.

Example 28

The crocodile leather bands and the cow leather bands (product model no. 59-S52979 for the cow leather and product model no. 59-T50736 for the crocodile leather) each containing hexavalent chromium described in Comparative Examples 1 and 2 were prepared. The hexavalent chromium contents in the crocodile leather and the cow leather were 8 ppm and 3 ppm, respectively.

The compounds shown in chemical formulae (3), (4), and (13) (0.5 g, 2.5 g, and 2.0 g, respectively) were mixed and dissolved in 500 g of a mixed solution of water and IPA (50% by weight:50% by weight) so that a hexavalent chromium treatment solution was obtained. The kinematic viscosity of the solution was 3.7 (cSt).

Each band was immersed in the obtained hexavalent chromium treatment solution so as to be impregnated therewith, followed by drying. Thus, two types of watchbands were obtained. For each band, the hexavalent chromium content was immediately determined in accordance with ISO 17075: 2008-02. As a result, it was confirmed that the hexavalent chromium content was at or below the detection limit (2 ppm). The bands were found to be non-toxic.

Subsequently, the bands were aged at 60° C. for 500 hours. Thus, watchbands for evaluation were obtained. For each band, the hexavalent chromium content was determined in accordance with ISO 17075: 2008-02. As a result, it was confirmed that the hexavalent chromium content was at or below the detection limit (2 ppm). The bands were found to be non-toxic. In addition, as a result of analysis of the total chromium content of each band using a fluorescent X-ray analyzer, the chromium contents in the crocodile leather and the cow leather were 7000 ppm and 16,000 ppm, respectively.

Then, the watchbands that had been aged were immersed in running water so as to be sufficiently impregnated with tap water. The resulting watchbands were aged at 80° C. for 500 hours so that watchbands for evaluation were obtained. For each band, the hexavalent chromium content was determined in accordance with ISO 17075: 2008-02. As a result, it was confirmed that the hexavalent chromium content was at or below the detection limit (2 ppm). The bands were found to be non-toxic.

It was revealed that if a hexavalent chromium treatment agent contains the compounds shown in chemical formulae (3) and (4), it is highly capable of penetrating leathers or leather articles and also capable of remaining in leathers or leather articles for a long period of time so as to achieve stable long-term reduction of hexavalent chromium. It was also revealed that such compounds are likely to be incorporated into leathers or leather articles before loss of color, and therefore, they are unlikely to cause color fading or discoloration and impair the color and texture of leathers or leather articles.

It was further revealed that when a hexavalent chromium treatment agent contains the compound shown in chemical formula (13), it can quickly detoxify the leather surface, thereby appropriately preventing the development of skin problems, allergy, and the like. It was further found that the compound is appropriately compatible with the compounds shown in chemical formulae (3) and (4), thereby preventing brownish discoloration or loss of color. It was still further found that the compound is highly degradable and therefore unlikely to cause coloration and impair the color and texture of leathers or leather articles.

Moreover, it was found that water and IPA used as solvents are excellent in miscibility, which makes it possible to avoid a fire in factories and achieve high-level safety. It was also found that the solvents with reasonable volatility can penetrate leather bands without impairing designability.

Example 29

Two types of leather bands were obtained in the manner described in Example 28 except that a hexavalent chromium treatment solution to be used was obtained by changing the amounts of the compounds shown in chemical formulae (3), (4), and (13) from 0.5 g to 0.75 g, from 2.5 g to 3.0 g, and from 2.0 g to 1.25 g, respectively.

After the leather bands were created, the hexavalent chromium content was determined in accordance with ISO 17075: 2008-02. As a result, the hexavalent chromium content was at or below the detection limit (2 ppm).

Subsequently, aging was conducted in the manner described in Example 28. For each obtained band, the hexavalent chromium content was determined in accordance with ISO 17075: 2008-02. As a result, the hexavalent chromium content was at or below the detection limit (2 ppm).

Then, treatment with running water was conducted in the manner described in Example 28. For each obtained band, the hexavalent chromium content was determined in accordance with ISO 17075: 2008-02. As a result, the hexavalent chromium content was at or below the detection limit (2 ppm).

Example 30

Two different leather bands were obtained in the manner described in Example 28 except that a hexavalent chromium treatment solution to be used was obtained by changing the amounts of the compounds shown in chemical formulae (3), (4), and (13) from 0.5 g to 0.25 g, from 2.5 g to 3.75 g, and from 2.0 g to 1.0 g, respectively.

After the leather bands were created, the hexavalent chromium content was determined in accordance with ISO 17075: 2008-02. As a result, the hexavalent chromium content was at or below the detection limit (2 ppm).

Subsequently, aging was conducted in the manner described in Example 28. For each obtained band, the hexavalent chromium content was determined in accordance with ISO 17075: 2008-02. As a result, the hexavalent chromium content was at or below the detection limit (2 ppm).

Then, treatment with running water was conducted in the manner described in Example 28. For each obtained band, the hexavalent chromium content was determined in accordance with ISO 17075: 2008-02. As a result, the hexavalent chromium content was at or below the detection limit (2 ppm).

Example 31

A hexavalent chromium treatment solution was obtained in the manner described in Example 28 except that the weight ratio of water and IPA in the mixed solution was changed from 50% by weight:50% by weight to 60% by weight:40% by weight.

After the leather bands were created, the hexavalent chromium content was determined in accordance with ISO 17075: 2008-02. As a result, the hexavalent chromium content was at or below the detection limit (2 ppm).

Subsequently, aging was conducted in the manner described in Example 28. For each obtained band, the hexavalent chromium content was determined in accordance with ISO 17075: 2008-02. As a result, the hexavalent chromium content was at or below the detection limit (2 ppm).

Then, treatment with running water was conducted in the manner described in Example 28. For each obtained band, the hexavalent chromium content was determined in accordance with ISO 17075: 2008-02. As a result, the hexavalent chromium content was at or below the detection limit (2 ppm).

Comparative Example 7

Bands were prepared using crocodile and cow leathers in the manner described in Example 28. The leathers were immersed in a 1/60 mol/l dichromate potassium solution in advance so as to be contaminated with hexavalent chromium. The contamination caused an increase in the hexavalent chromium content in leathers by 70 ppm.

The compound shown in chemical formula (13) in an amount of 5.0 g was mixed and dissolved in 500 g of a mixed solution of water and IPA (50% by weight:50% by weight) so that a solution was obtained.

Each band was immersed in the obtained solution so as to be impregnated therewith, followed by drying. Thus, watchbands were obtained. For each band, the hexavalent chromium content was immediately determined in accordance with ISO 17075: 2008-02. As a result, the hexavalent chromium content was at or below the detection limit (2 ppm).

Subsequently, the bands were aged at 60° C. for 500 hours. Thus, watchbands for evaluation were obtained. For each band, the hexavalent chromium content was determined in accordance with ISO 17075: 2008-02. As a result, the hexavalent chromium content was at or below the detection limit (2 ppm).

Then, the watchbands that had been aged were immersed in running water so as to be sufficiently impregnated with tap water. The resulting watchbands were aged at 80° C. for 500 hours so that watchbands for evaluation were obtained. For each band, the hexavalent chromium content was determined in accordance with ISO 17075: 2008-02. As a result, hexavalent chromium was detected.

A comparison between Examples 28 to 31 and Comparative Example 7 revealed that the hexavalent chromium treatment agent has immediate effectivity and is capable of stably remaining in bands for a long period of time for detoxification. It was also revealed that bands treated with the hexavalent chromium treatment agent do not cause hexavalent chromium to leach out for a long period of time even when exposed to moisture due to sweat or rain, and therefore, they are human body-friendly and environment-friendly products.

Example 32

Bands were prepared using crocodile and cow leathers in the manner described in Example 28.

The compounds shown in chemical formulae (4) and (13) (3.0 g and 2.0 g, respectively) were mixed and dissolved in 500 g of a mixed solution of water and IPA (50% by weight: 50% by weight) so that a hexavalent chromium treatment solution was obtained.

The obtained hexavalent chromium treatment solution was applied to the band surfaces using a spray and dried at room temperature. Thus, two types of treated leather bands were obtained. For each band, the hexavalent chromium content was immediately determined in accordance with ISO 17075: 2008-02. As a result, the hexavalent chromium content was at or below the detection limit (2 ppm).

Subsequently, aging was conducted in the manner described in Example 28. For each obtained band, the hexavalent chromium content was determined in accordance with ISO 17075: 2008-02. As a result, the hexavalent chromium content was at or below the detection limit (2 ppm).

Example 33

Bands were prepared using crocodile and cow leathers in the manner described in Example 28.

The compounds shown in chemical formulae (3) and (13) (2.5 g each) were mixed and dissolved in 500 g of a mixed solution of water and IPA (50% by weight: 50% by weight) so that a hexavalent chromium treatment solution was obtained.

The obtained hexavalent chromium treatment solution was applied to the band surfaces using a spray and dried at room temperature. Thus, two types of treated leather bands were obtained. For each band, the hexavalent chromium content was immediately determined in accordance with ISO 17075: 2008-02. As a result, the hexavalent chromium content was at or below the detection limit (2 ppm).

Subsequently, aging was conducted in the manner described in Example 28. For each obtained band, the hexavalent chromium content was determined in accordance with ISO 17075: 2008-02. As a result, the hexavalent chromium content was at or below the detection limit (2 ppm).

Then, treatment with running water was conducted in the manner described in Example 28. For each obtained band, the hexavalent chromium content was determined in accordance with ISO 17075: 2008-02. As a result, the hexavalent chromium content was at or below the detection limit (2 ppm).

Example 34

Surface treatment was examined using a cow leather that had been confirmed to be colorable. As shown in FIG. 1, red colored matter was eluted when the leather was immersed in the mixed solution of water and IPA (50% by weight: 50% by weight).

Leather bands were prepared using the leather in the manner described in Comparative Examples 1 and 2. The leather was immersed in a 1/60 mol/l dichromate potassium solution in advance so as to be contaminated with hexavalent chromium. The contamination caused an increase in the hexavalent chromium content in the leather by 70 ppm.

A hexavalent chromium treatment solution was obtained in the manner described in Example 28 except that a hexavalent chromium treatment solution to be used was obtained by changing the mixed solution of water and IPA to water alone. The obtained treatment solution was applied to the leather bands using a spray and dried at room temperature. Thus, treated leather band sheets were obtained.

As a result of visual observation of the bands, it was found that color fading or discoloration did not take place on the leather surfaces, and therefore, the color and texture were not impaired.

Example 35

Surface treatment was examined using a cow leather that had been confirmed to be colorable. As shown in FIG. 2, green colored matter was eluted when the leather was immersed in the mixed solution of water and IPA (50% by weight: 50% by weight).

Leather bands treated with the hexavalent chromium treatment solution were prepared using the leather in the manner described in Example 34.

As a result of visual observation of the bands, it was found that color fading or discoloration did not take place on the leather surfaces, and therefore, the color and texture were not impaired.

Example 36

The crocodile leather bands and the cow leather bands (product model no. 59-S52979 for the cow leather and product model no. 59-T50736 for the crocodile leather) each containing hexavalent chromium described in Comparative Examples 1 and 2 were prepared. The hexavalent chromium contents in the crocodile leather and the cow leather were 8 ppm and 3 ppm, respectively.

The compounds shown in chemical formulae (3) and (4) in amounts of 0.3 g and 0.7 g, respectively, were mixed and dissolved in 100 g of a mixed solution of water and IPA (50% by weight:50% by weight) so that a hexavalent chromium treatment solution was obtained.

Each band was immersed in the obtained hexavalent chromium treatment solution so as to be impregnated therewith, followed by drying. Thus, two types of watchbands were obtained.

Subsequently, the bands were aged at 60° C. for 500 hours. Thus, watchbands for evaluation were obtained. For each band, the hexavalent chromium content was determined in accordance with ISO 17075: 2008-02. As a result, the hexavalent chromium content was at or below the detection limit (2 ppm).

Then, the watchbands that had been aged were immersed in running water so as to be sufficiently impregnated with tap water. The resulting watchbands were aged at 80° C. for 500 hours so that watchbands for evaluation were obtained. For each band, the hexavalent chromium content was determined in accordance with ISO 17075: 2008-02. As a result, the hexavalent chromium content was at or below the detection limit (2 ppm). Also, for each band, the total chromium content was analyzed using a fluorescent X-ray analyzer after aging. As a result, the content for the crocodile leather was 7000 ppm and that for the cow leather was 16,000 ppm.

The invention claimed is:

1. A leather or leather article, containing at least:
an organic compound (A) having a structure shown in chemical formula (1) below and hydroxyphenyl, wherein said organic compound (A) does not have reactive functional groups of an aldehyde and carboxyl, the organic compound acting to reduce hexavalent chromium to trivalent chromium; and
trivalent chromium, wherein the hexavalent chromium content is less than 3 ppm:

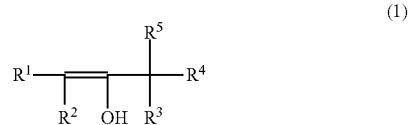

(1)

(where $R^1$, $R^2$, $R^3$, $R^4$ and $R^5$ are each independently a substituent composed of at least one selected from C, H and O, and $R^1$ or $R^2$ may be combined with $R^3$, $R^4$, or $R^5$ to form a ring),
wherein the organic compound (A) contains:
(i) gallic acid ester; and
(ii) at least one compound selected from tannic acid and a derivative thereof.

2. The leather or leather article according to claim 1, wherein the total chromium content obtained by X-ray fluorometry is not less than 5000 ppm.

3. The leather or leather article according to claim 1, wherein the organic compound (A) includes a compound having a structure shown in chemical formula (1) and dihydroxyphenyl or trihydroxyphenyl, wherein said compound does not have reactive functional groups of an aldehyde and carboxyl, the compound acting to reduce hexavalent chromium to trivalent chromium.

4. The leather or leather article according to claim 3, wherein the organic compound (A) includes a compound having a structure shown in chemical formula (1) and 1,2,3-trihydroxyphenyl, wherein said compound does not have reactive functional groups of an aldehyde and carboxyl, the compound acting to reduce hexavalent chromium to trivalent chromium.

5. The leather or leather article according to claim 1, wherein the compound (ii) is tannic acid.

6. A leather or leather article, containing at least:
an organic compound (A) having a structure shown in chemical formula (1) below and hydroxyphenyl, wherein said organic compound (A) does not have reactive functional groups of an aldehyde and carboxyl, the organic compound acting to reduce hexavalent chromium to trivalent chromium;
an organic compound (B) having a structure shown in chemical formula (1) wherein said organic compound (B) does not have a hydroxyphenyl, aldehyde, and carboxyl, the compound (B) acting to reduce hexavalent chromium to trivalent chromium; and
trivalent chromium, wherein the hexavalent chromium content is less than 3 ppm:

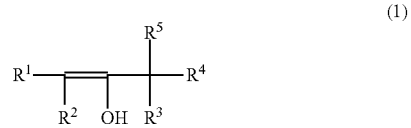

(1)

(where R1, R2, R3, R4 and R5 are each independently a substituent composed of at least one selected from C, H and O, and R1 or R2 may be combined with R3, R4, or R5 to form a ring).

7. The leather or leather article according to claim 6, wherein the organic compound (B) is at least one compound selected from the group consisting of ascorbic acid, a derivative of ascorbic acid, erythorbic acid, and a derivative of erythorbic acid.

8. A hexavalent chromium treatment agent, containing at least:
an organic compound (A) having a structure shown in chemical formula (1) and hydroxyphenyl, wherein said organic compound (A) does not have reactive functional groups of an aldehyde and carboxyl, the organic compound acting to reduce hexavalent chromium to trivalent chromium; and
an organic compound (B) having a structure shown in chemical formula (1) wherein said organic compound (B) does not have a hydroxyphenyl, aldehyde, and carboxyl, the organic compound acting to reduce hexavalent chromium to trivalent chromium:

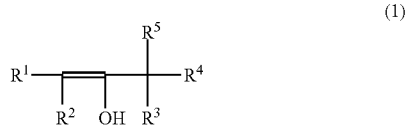

(where R1, R2, R3, R4 and R5 are each independently a substituent composed of at least one selected from C, H and O, and R1 or R2 may be combined with R3, R4, or R5 to form a ring).

9. The hexavalent chromium treatment agent according to claim 8, wherein the organic compound (B) is at least one compound selected from the group consisting of ascorbic acid, a derivative of ascorbic acid, erythorbic acid, and a derivative of erythorbic acid.

10. The hexavalent chromium treatment agent according to claim 8, wherein the organic compounds (A) and (B) are contained at a weight percent ratio of 50-90:10-50 (provided that the sum of A and B equals to 100% by weight).

11. The hexavalent chromium treatment agent according to claim 8, which is an aqueous solution containing a solvent consisting of water.

12. The hexavalent chromium treatment agent according to claim 8, which further contains C1-C3 alcohol.

13. The hexavalent chromium treatment agent according to claim 12, which further contains water.

14. The hexavalent chromium treatment agent according to claim 8, which further contains water and C1-C3 alcohol, wherein the water and alcohol are contained at a weight percent ratio of 20-80:20-80 (provided that the sum of both equals to 100% by mass), and wherein the organic compounds (A) and (B) are dissolved in the water and alcohol.

15. The hexavalent chromium treatment agent according to claim 8, which further contains at least one solvent selected from hexane and heptane.

16. The hexavalent chromium treatment agent according to claim 15, which further contains C1-C3 alcohol.

17. The hexavalent chromium treatment agent according to claim 8, which further contains C1-C3 alcohol, and hexane and/or heptane, wherein the alcohol and hexane and/or heptane are contained at a weight percent ratio of 20-80:20-80 (provided that the sum of both equals to 100% by mass), and wherein the organic compounds (A) and (B) are dissolved in the alcohol and hexane and/or heptane.

18. The hexavalent chromium treatment agent according to claim 11, which is capable of permeating a leather or leather article.

19. The hexavalent chromium treatment agent according to claim 11, wherein kinetic viscosity at 25° C. is from 0.001 (cSt) to less than 5 (cSt).

20. The hexavalent chromium treatment agent according to claim 8, wherein the organic compound (A) includes a compound having a structure shown in chemical formula (1) and dihydroxyphenyl or trihydroxyphenyl, wherein said compound does not have reactive functional groups of an aldehyde and carboxyl, the compound acting to reduce hexavalent chromium to trivalent chromium.

21. The hexavalent chromium treatment agent according to claim 20, wherein the organic compound (A) includes a compound having a structure shown in chemical formula (1) and 1,2,3-trihydroxyphenyl, wherein said compound does not have reactive functional groups of an aldehyde and carboxyl, the compound acting to reduce hexavalent chromium to trivalent chromium.

22. The hexavalent chromium treatment agent according to claim 21, wherein the organic compound (A) contains:
(i) gallic acid ester; and
(ii) at least one compound selected from tannic acid and a derivative thereof.

23. The hexavalent chromium treatment agent according to claim 22, wherein the compound (ii) is tannic acid.

24. The hexavalent chromium treatment agent according to claim 22, wherein the compound (i), the compound (ii) and the organic compound (B) are contained at a weight percent ratio of 1-20:30-89:10-50 (provided that the sum of (i), (ii), and (B) equals to 100% by weight).

25. The hexavalent chromium treatment agent according to claim 8, which is used for a leather or leather article.

26. A method for treating hexavalent chromium contained in a crude leather or crude leather article, comprising bringing a crude leather containing hexavalent chromium or a crude leather article containing hexavalent chromium into contact with the hexavalent chromium treatment agent according to claim 8.

27. A method for treating hexavalent chromium contained in a crude leather or crude leather article, comprising bringing a crude leather containing hexavalent chromium or a crude leather article containing hexavalent chromium into contact with the hexavalent chromium treatment agent according to claim 8 by means of spraying, atomizing, dipping, coating, or immersion.

28. The method for treating hexavalent chromium contained in a crude leather or crude leather article according to claim 26, wherein the total chromium content in the crude leather or crude leather article, obtained by X-ray fluorometry, is not less than 5000 ppm.

29. A method for producing a leather or leather article, comprising bringing a crude leather containing hexavalent chromium or a crude leather article containing hexavalent chromium into contact with the hexavalent chromium treatment agent according to claim 8, wherein the hexavalent chromium content is less than 3 ppm.

30. The method for producing a leather or leather article according to claim 29, wherein the total chromium content in the leather or leather article, obtained by X-ray fluorometry, is not less than 5000 ppm.

31. A hexavalent chromium treatment agent, containing at least:
an organic compound (A) having a structure shown in chemical formula (1) and hydroxyphenyl, wherein said organic compound (A) does not have reactive functional groups of an aldehyde and carboxyl, the organic compound acting to reduce hexavalent chromium to trivalent chromium; and at least two solvents selected from the group consisting of water, C1-C3 alcohol, hexane, and heptane, wherein the hexavalent chromium treatment agent is capable of permeating a leather or leather article:

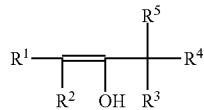
(1)

(where $R^1$, $R^2$, $R^3$, $R^4$ and $R^5$ are each independently a substituent composed of at least one selected from C, H and O, and $R^1$ or $R^2$ may be combined with $R^3$, $R^4$, or $R^5$ to form a ring).

32. The hexavalent chromium treatment agent according to claim 31, which further contains an organic compound (B) having a structure shown in chemical formula (1), wherein said organic compound (B) does not have a hydroxyphenyl, aldehyde, and carboxyl, the organic compound acting to reduce hexavalent chromium to trivalent chromium.

33. The hexavalent chromium treatment agent according to claim 31, wherein kinetic viscosity at 25° C. is from 0.001 (cSt) to less than 5 (cSt).

* * * * *